US011124550B2

(12) United States Patent
Petrou et al.

(10) Patent No.: US 11,124,550 B2
(45) Date of Patent: Sep. 21, 2021

(54) PROTEINACEOUS MOLECULES AND METHODS OF USE

(71) Applicants: The University of Queensland, St Lucia (AU); The Florey Institute of Neuroscience and Mental Health, Parkville (AU); The Johns Hopkins University, Baltimore, MD (US); The Regents of the University of California, Oakland, CA (US)

(72) Inventors: Steven Petrou, Eltham (AU); Glenn King, Chapel Hill (AU); Frank Bosmans, Annapolis, MD (US); David Julius, Walnut Creek, CA (US); Jeremiah Osteen, San Francisco, CA (US); Chuchu Zhang, Brookline, MA (US)

(73) Assignees: THE UNIVERSITY OF QUEENSLAND, Queensland (AU); THE JOHNS HOPKINS UNIVERSITY, Baltimore, MD (US); THE FLOREY INSTITUTE OF NEUROSCIENCE AND MENTAL HEALTH, Victoria (AU); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/061,074

(22) PCT Filed: Dec. 9, 2016

(86) PCT No.: PCT/AU2016/051213
§ 371 (c)(1),
(2) Date: Jun. 11, 2018

(87) PCT Pub. No.: WO2017/096431
PCT Pub. Date: Jun. 15, 2017

(65) Prior Publication Data
US 2020/0299339 A1 Sep. 24, 2020

Related U.S. Application Data

(60) Provisional application No. 62/265,037, filed on Dec. 9, 2015.

(51) Int. Cl.
| | | |
|---|---|---|
| *A61K 38/17* | (2006.01) | |
| *C07K 14/435* | (2006.01) | |
| *A61P 25/08* | (2006.01) | |
| *C12N 5/0793* | (2010.01) | |
| *A61K 38/00* | (2006.01) | |

(52) U.S. Cl.
CPC .... *C07K 14/43518* (2013.01); *A61K 38/1767* (2013.01); *A61P 25/08* (2018.01); *C12N 5/0619* (2013.01); *A61K 38/00* (2013.01)

(58) Field of Classification Search
CPC ...... A61K 38/1767; A61P 25/00; A61P 25/08; A61P 25/10; A61P 25/12; A61P 25/28; C07K 14/43518
See application file for complete search history.

(56) References Cited

U.S. PATENT DOCUMENTS

| | | |
|---|---|---|
| 2013/0036482 A1 | 2/2013 | Ohmori et al. |
| 2016/0235718 A1* | 8/2016 | Baraban ............. A61K 31/4166 |

FOREIGN PATENT DOCUMENTS

| | | |
|---|---|---|
| WO | 2010/104114 A1 | 9/2010 |
| WO | 2013/134734 A2 | 9/2013 |

OTHER PUBLICATIONS

International Search Report for PCT/AU2016/051213 dated Mar. 15, 2017, 4 pages.
International Preliminary Report on Patentability and Written Opinion for PCT/AU2016/051213 dated Jun. 12, 2018, 6 pages.
Jensen, et al. "Therapeutic potential of NaV1.1 activators", Trends in Pharmacological Sciences, 35, No. 3:113-118 (2014).
Kaczorowski, et al. "Ion Channels as Drug Targets: The Next GPCRs", J. Gen. Physiol., 131 No. 5:399-405 (2008).
Klint, et al. "Spider-venom peptides that target voltage-gated sodium channels: Pharmacological tools and potential therapeutic leads", Toxicon 60:478-491 (2012).
Osteen, et al. "Selective spider toxins reveal a role for the Nav1.1 channel in mechanical pain", Nature, 534:494-509 (2016).
Saez, et al. "Spider-Venom Peptides as Therapeutics", *Toxins*, 2:2851-2871 (2010).
Verret, et al. "Inhibitory Interneuron Deficit Links Altered Network Activity and Cognitive Dysfunction in Alzheimer Model", Cell 149; 708-721 (2012).
Clare, et al. "Voltage-gated sodium channels as therapeutic targets", vol. 5, No. 11:506-520 (2000).
Escoubas, et al. "Novel Tarantula Toxins for Subtypes of Voltage-Dependent Potassium Channels in the Kv2 and Kv4 Subfamilies", Molecular Pharmacology, vol. 62, No. 1:48-57 (2002).

* cited by examiner

*Primary Examiner* — Jeffrey E. Russel
(74) *Attorney, Agent, or Firm* — Nixon & Vanderhye, P.C.

(57) ABSTRACT

This invention relates to peptides and their use for modulating sodium channels. More particularly, the present invention relates to peptides and their use in methods of enhancing Na$_v$1.1 activity and for treating or preventing conditions associated with Na$_v$1.1 activity.

29 Claims, 15 Drawing Sheets
Specification includes a Sequence Listing.

PROTEINACEOUS MOLECULES AND METHODS OF USE

This application is the U.S. national phase of International Application No. PCT/AU2016/051213 filed Dec. 9, 2016 which designated the U.S. and claims the benefit of U.S. Provisional Application No. 62/265,037 filed Dec. 9, 2015.

STATEMENT REGARDING FEDERALLY SPONSORED RESEARCH AND DEVELOPMENT

This invention was made with government support under grant Nos. NS065071, F32 NS081907 and R01 NS091352 awarded by the National Institutes of Health. The government has certain rights in the invention.

REFERENCE TO SEQUENCE LISTING SUBMITTED ELECTRONICALLY

The content of the electronically submitted sequence listing (Name: 0659_0201_Sequence_Listing_22APR2021_ST25.txt; Size: 7.81 kilobytes; and Date of Creation: Apr. 22, 2021) filed on Apr. 22, 2021 is incorporated herein by reference in its entirety.

FIELD OF THE INVENTION

This invention relates to peptides and their use for modulating sodium channels. More particularly, the present invention relates to peptides and their use in methods of enhancing $Na_v1.1$ activity and for treating or preventing conditions associated with $Na_v1.1$ activity.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Venomous animals produce venom rich in bioactive components that have evolved to specifically and potently modulate a wide range of ion channels and receptors. Due to these exquisite properties, venom components have found use in the treatment and management of several conditions. For example, the analgesic drug PRIALT® (ziconotide) is a peptide from the venom of the marine cone snail *Conus magus*.

Spider venoms are predominantly comprised of peptides, with some venoms containing greater than 1000 novel peptides. These venoms contain a significant number of peptides that modulate the activity of neuronal ion channels and receptors, such as voltage-gated potassium ($K_v$), calcium ($Ca_v$) and sodium ($Na_v$) channels, which is not surprising due to the paralytic function of spider venom (Saez, et al. (2010) *Toxins*, 2:2851-71).

Spider venom peptides typically adopt an inhibitor cystine knot conformation, which provides them with extraordinary chemical, thermal and biological stability. The inhibitor cystine knot comprises a ring formed by two disulfide bonds and the intervening peptide backbone, with a third disulfide bond piercing the ring, forming a pseudo-knot. The stability resulting from this conformation is advantageous for the development of peptide therapeutics.

Voltage-gated sodium channels ($Na_v$) are complex transmembrane proteins comprised of a pore-forming α-subunit and accessory β-subunits that play an essential role in the initiation and propagation of action potentials in excitable cells. $Na_v$ channels open to permit influx of sodium ions when the membrane potential is depolarized and close on repolarization. They also close on continuous depolarization by a process termed inactivation, which leaves the channel refractory (i.e. unable to open again for a period of time).

To date, apart from the related $Na_x$, which has been suggested to function as a sodium sensor (Shimizu, et al. (2007) *Neuron*, 54(1): 59-72; Hiyama, et al. (2002) *Nat Neurosci*, 5(6): 511-512), nine isoforms termed $Na_v1.1$-$Na_v1.9$ have been functionally defined as sodium-selective ion channels (Yu and Catterall (2003) *Genome Biol*, 4(3): 207). Their distinct tissue distribution as well as amenability to modulation by toxins and drugs has led to significant interest in $Na_v$ channels as therapeutic targets in a number of poorly treated conditions, ranging from epilepsy to cardiac arrhythmias and pain (Clare, et al. (2000) *Drug Discov Today*, 5(11): 506-520).

In contrast to $Na_v$ inhibitors which have been developed and approved as drugs to treat a variety of conditions, compounds which enhance $Na_v$ activity typically are not considered to be therapeutically relevant due to a perceived high risk of toxicity and adverse effects. Recently this opinion has been changing in relation to compounds which enhance $Na_v1.1$ activity, due to the discovery that this $Na_v$ subtype comprises the majority of the sodium current in specific inhibitory interneurons and only plays a modest role in excitatory neurons. Inhibitory interneurons synthesise and release γ-aminobutyric acid (GABA), which is the major inhibitory neurotransmitter in the brain and, thus, these interneurons play an important role in the regulation of excitability of neuronal populations in the central nervous system (Jensen, et al. (2014) *Trends Pharmacol Sci*, 35(3): 113-118).

There are several conditions associated with $Na_v1.1$ activity, including epilepsy such as Dravet syndrome, generalised epilepsy with febrile seizures plus, borderline severe myoclonic epilepsy of infancy and intractable childhood epilepsy with generalised tonic-clonic seizures; Alzheimer's disease; autism spectrum disorders such as autism; and schizophrenia. Thus, compounds that enhance $Na_v1.1$ activity may be useful for these indications (Jensen, et al. (2014) *Trends Pharmacol Sci*, 35(3): 113-118; Verret, et al. (2012) *Cell*, 149: 708-721).

Accordingly, there exists a need for new therapeutic agents which enhance $Na_v1.1$ activity and which may be useful in the treatment and prevention of conditions associated with $Na_v1.1$ activity.

SUMMARY OF THE INVENTION

The present invention is predicated in part on the discovery of peptides that modulate $Na_v$ channels, particularly $Na_v1$. These peptides may be useful for enhancing $Na_v1.1$ activity and may be useful in the treatment or prevention of conditions associated with $Na_v1.1$ activity.

In one aspect of the present invention, there is provided a method of enhancing $Na_v1.1$ activity, comprising contacting a $Na_v1.1$ expressing cell with an isolated, synthetic or recombinant peptide comprising, consisting or consisting essentially of SEQ ID NO: 1:

[SEQ ID NO: 1]
Xaa₁CRYLFGGCXaa₂Xaa₃TXaa₄DCCKHLXaa₅CRXaa₆DXaa₇Xaa₈
YCZ₁ wherein:
Xaa₁ is absent or is selected from acidic amino acid residues, including Asp and Glu;
Xaa₂ is selected from small amino acid residues, including Ser and Thr, and basic amino acid residues, including Arg, His and Lys;
Xaa₃ is selected from selected from small amino acid residues, including Ser and Thr;
Xaa₄ is selected from small amino acid residues, including Ser, Thr, Ala and Gly;
Xaa₅ is selected from small amino acid residues, including Ser, Thr, Ala and Gly;
Xaa₆ is selected from small amino acid residues, including Ser and Thr;
Xaa₇ is selected from aromatic amino acid residues, including Phe, Trp and Tyr, and hydrophobic amino acid residues, including Ile, Leu and Val;
Xaa₈ is selected from aromatic amino acid residues, including Phe, Trp and Tyr, and basic amino acid residues, including Arg, His and Lys; and
Z₁ is absent or is an amino acid sequence of SEQ ID NO: 2:

[SEQ ID NO: 2]
AWDGTFXaa₉ wherein:
Xaa₉ is absent or is a small amino acid residue, including Ser and Thr.

In another aspect of the present invention, there is provided a method of treating or preventing a condition in respect of which enhancing Na$_v$1.1 activity is associated with effective treatment, comprising administration of an isolated, synthetic or recombinant peptide comprising, consisting or consisting essentially of SEQ ID NO: 1.

In yet another aspect of the present invention, there is provided an isolated, synthetic or recombinant peptide comprising, consisting or consisting essentially of SEQ ID NO: 1:

[SEQ ID NO: 1]
Xaa₁CRYLFGGCXaa₂Xaa₃TXaa₄DCCKHLXaa₅CRXaa₆DXaa₇Xaa₈
YCZ₁ wherein:
Xaa₁ is absent or is selected from acidic amino acid residues, including Asp and Glu;
Xaa₂ is selected from small amino acid residues, including Ser and Thr, and basic amino acid residues, including Arg, His and Lys;
Xaa₃ is selected from selected from small amino acid residues, including Ser and Thr;
Xaa₄ is selected from small amino acid residues, including Ser, Thr, Ala and Gly;
Xaa₅ is selected from small amino acid residues, including Ser, Thr, Ala and Gly;
Xaa₆ is selected from small amino acid residues, including Ser and Thr;
Xaa₇ is selected from aromatic amino acid residues, including Phe, Trp and Tyr, and hydrophobic amino acid residues, including Ile, Leu and Val;
Xaa₈ is selected from aromatic amino acid residues, including Phe, Trp and Tyr, and basic amino acid residues, including Arg, His and Lys;
Z₁ is absent or is an amino acid sequence of SEQ ID NO: 2:

[SEQ ID NO: 2]
AWDGTFXaa₉ wherein:
Xaa₉ is absent or is a small amino acid residue, including Ser and Thr; and wherein the peptide is other than a peptide consisting of the amino acid sequence of SEQ ID NO: 4:

[SEQ ID NO: 4]
ECRYLFGGCSSTSDCCKHLSCRSDWKYCAWDGTFS.

DETAILED DESCRIPTION OF THE INVENTION

1. Definitions

Figure 1:
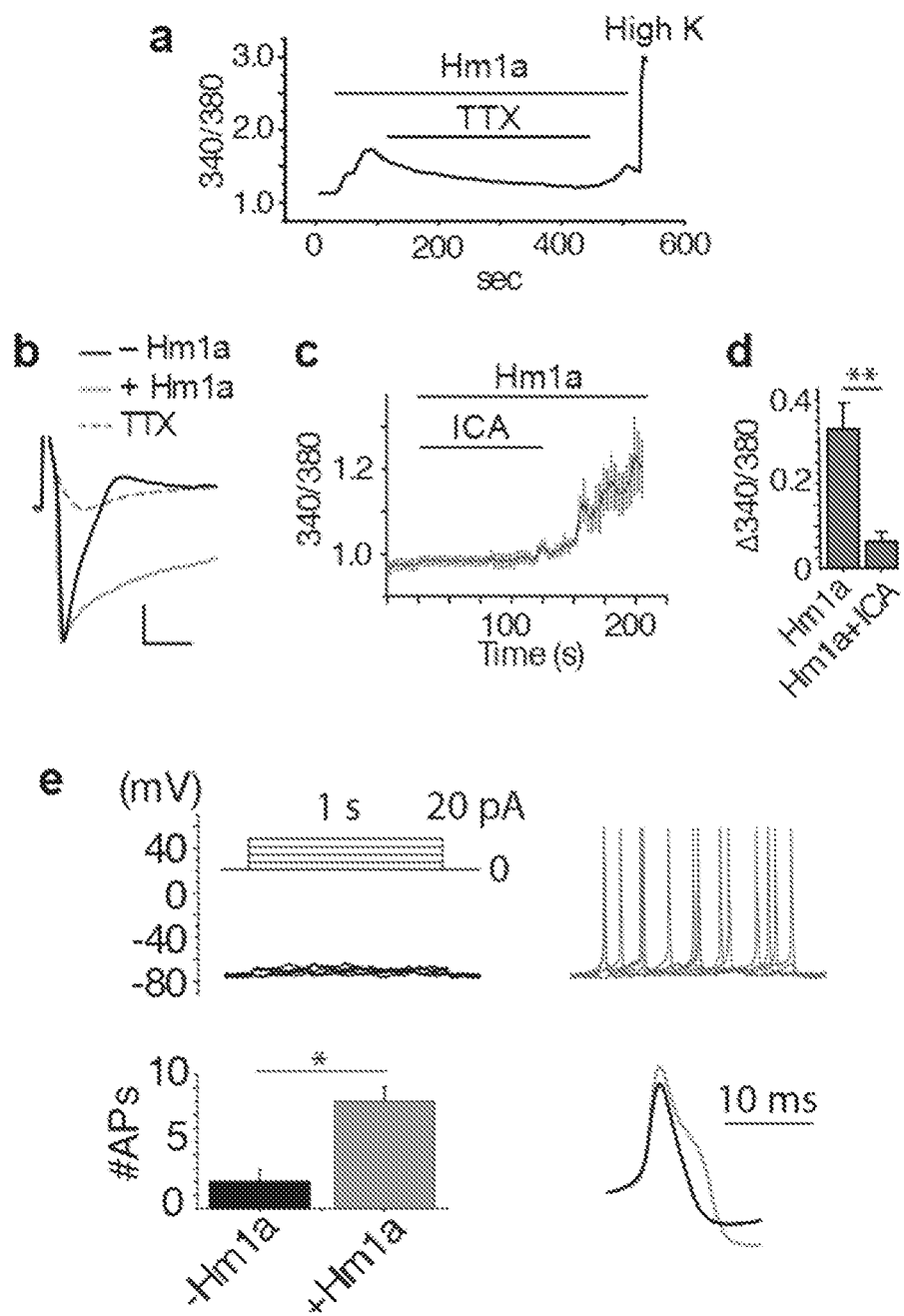
FIG. 1 Effect of Hm1a on Na 1.1 in sensory neurons. a. Average ratiometric calcium responses from Hm1a-sensitive embryonic rat dorsal root ganglion (DRG) neurons. Hm1a (500 nM) was applied in the presence or absence of tetrodotoxin (TTX, 10 µM), as indicated. b. Representative whole-cell patch clamp recording from Hm1a-sensitive P0 mouse trigeminal (TG) neuron. All Hm1a responsive neurons (15/15 as identified by calcium imaging) displayed a similar effect of toxin on sodium current inactivation. Vertical scale bar=0.5 nA; horizontal scale bar=5 ms. c. Average Hm1a-evoked calcium response in the presence of ICA-121431 (500 nM) and after washout (n=11). d. Quantification of maximum calcium signal from Hm1a-responsive cells with or without ICA-121431 (n=25). e. (Top panels) Representative current clamp recording from mouse TG neuron in the absence (black, left panel) or presence (grey, right panel) of Hm1a (500 nM). (Bottom left) Quantification of action potentials elicited by a 1 s, 20 pA current injection before or after exposure to Hm1a (500 nM, n=4). (Bottom right) Representative action potentials before (black) and after (grey) exposure to Hm1a during a 20 pA current injection. *$p<0.05$ and **$p<0.001$ based on student's t-test. Error bars represent mean±SEM.
Figure 2:
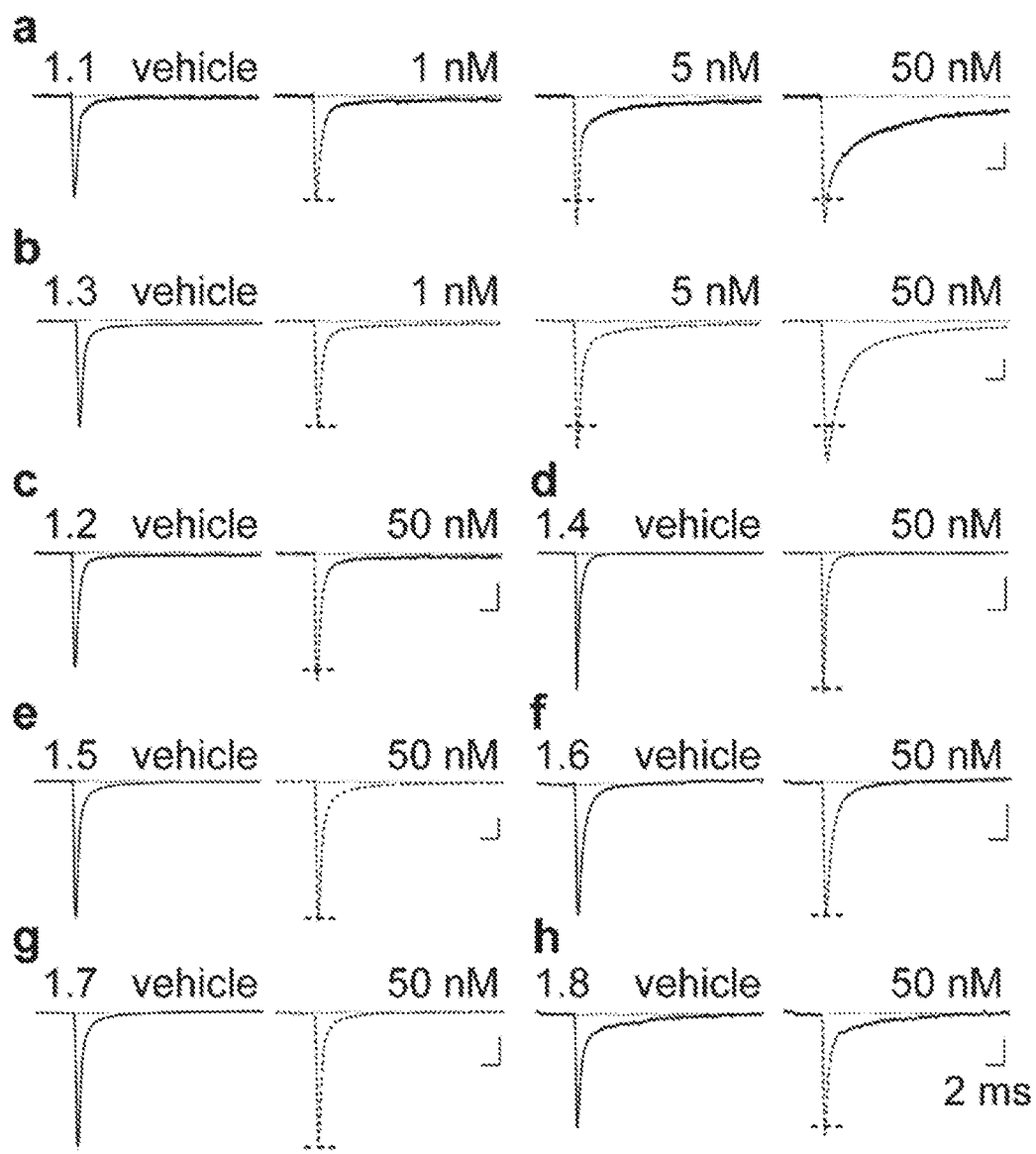
FIG. 2 Effect of Hm1a on human voltage-gated sodium channel subtypes, hNa$_v$1.1-hNa$_v$1.8, stably expressed in HEK293T or CHO cells. a. Representative raw current traces for hNa$_v$1.1 in the presence of vehicle and 1, 5 or 50 nM Hm1a. b. Representative raw current traces for hNa$_v$1.3 in the presence of vehicle and 1, 5 or 50 nM Hm1a. c-h. Representative raw current traces for hNa$_v$1.2, hNa$_v$1.4, hNa$_v$1.5, hNa$_v$1.6, hNa$_v$1.7 and hNa$_v$1.8 in the presence of vehicle and 50 nM Hm1a. All traces are averages of multiple sweeps over a 30 s periods. Scale bars a. c. h. 100 pA, b. f. 200 pA and d. e. g. 500 pA.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to conditions (e.g. amounts, concentrations, time, etc.) that vary by as much as 30%, especially by as much as 20%, and more especially by as much as 10%, 9%, 8%, 7%, 6%, 5%, 4%, 3%, 2% or 1% to a specified condition.

As used herein, the term "and/or" refers to and encompasses any and all possible combinations of one or more of the associated listed items, as well as the lack of combinations when interpreted in the alternative (or).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, the use of the term "comprising" and the like indicates that the listed integers are required or mandatory, but that other integers are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. In specific embodiments, the term "consisting essentially of", in the context of a specific amino acid sequence disclosed herein, includes within its scope about 1 to about 50 optional amino acids (and all integer optional amino acids in between) upstream of the specific amino acid sequence and/or about 1 to about 50 optional amino acids (and all integer optional amino acids in between) downstream of the specific amino acid sequence.

As used herein, the term "condition" refers to an abnormality in the physical state of the body as a whole or one of its parts.

As used herein, the terms "inhibitor cystine knot" and "inhibitor cystine knot motif" refer to a structural motif wherein a ring formed by two disulfide bonds and the intervening peptide backbone is pierced by a third disulfide bond.

As used herein, the term "dosage unit form" refers to physically discrete units suited as unitary dosages for the subject to be treated, each unit containing a predetermined quantity of active material calculated to produce the desired therapeutic effect in association with the required pharmaceutically acceptable vehicle. As used herein, the term "enhancing $Na_v1.1$ activity" and grammatical variants thereof refers to an increase in the conduction of sodium ions through $Na_v1.1$. For example, peptides that enhance $Na_v1.1$ activity may include peptides that initiate the transition of $Na_v1.1$ from a resting (non-conducting) state to the activated (conducting) state, and peptides that delay or prevent inactivation of $Na_v1.1$ and/or peptides that alter voltage dependence of activation or inactivation.

As used herein, the term "isolated" refers to material that is substantially or essentially free from components that normally accompany it in its native state. For example, an "isolated peptide" refers to in vitro isolation and/or purification of a peptide from its natural cellular environment and from association with other components of the cell.

The term "inactivation" is used herein to refer to an ion channel moving into the inactivated state. In particular embodiments, the term "inactivation" refers only to fast inactivation. Transitions into and out of the fast inactivated state are in the time frame of milliseconds as opposed to slow inactivation which occurs in the tens of seconds time frame.

The term "inactivated" as used herein, refers to a voltage dependent ion channel in a particular non-conducting conformational state. The inactivated state is usually the preferred state at elevated transmembrane potentials. At low transmembrane potentials, the inactivated state is unstable and relaxes to the closed state.

The term "loss of function mutation" is used herein to refer to one or more mutations in a gene sequence that results in the gene product having reduced or no function i.e. the gene product is partially or wholly missing normal function.

As used herein, the term "$Na_v1.1$" refers to any subunit of $Na_v1.1$, unless expressly stated.

The term "$Na_v1.1$ expressing cell" is used herein to refer to a vertebrate cell, particularly a mammalian or avian cell, especially a mammalian cell, that expresses at least one $Na_v1.1$ channel. The cell may be a vertebrate cell, such as a primate cell; an avian cell; a livestock animal cell such as a sheep cell, cow cell, horse cell, deer cell, donkey cell and pig cell; a laboratory test animal cell such as a rabbit cell, mouse cell, rat cell, guinea pig cell and hamster cell; a companion animal cell such as a cat cell and dog cell; and a captive wild animal cell such as a fox cell, deer cell and dingo cell. In particular embodiments, the $Na_v1.1$ expressing cell is a human cell. In specific embodiments, the $Na_v1.1$ expressing cell is a neuronal cell, especially an interneuron, most especially an inhibitory interneuron.

The term "operably linked" as used herein means placing a structural gene under the regulatory control of a regulatory element including, but not limited to, a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e. the genes from which it is derived. As used herein, the terms "peptide", "protein" and "proteinaceous molecule" are used interchangeably to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject peptides are particularly useful. Included within the definition are, for example, peptides containing one or more analogues of an amino acid including, for example, unnatural amino acids or peptides with substituted linkages.

As used herein, the terms "salts" and "prodrugs" include any pharmaceutically acceptable salt, ester, hydrate or any other compound which, upon administration to the recipient, is capable of providing (directly or indirectly) a peptide of the invention, or an active metabolite or residue thereof. Suitable pharmaceutically acceptable salts include salts of pharmaceutically acceptable inorganic acids such as hydrochloric, sulfuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Also, basic nitrogen-containing groups may be quaternized with such agents as lower alkyl halides, such as methyl, ethyl, propyl and butyl chlorides, bromides and iodides; dialkyl sulfates such as dimethyl and diethyl sulfate; and others. However, it will be appreciated that non-pharmaceutically acceptable salts also fall within the scope of the invention since these may be useful in the preparation of pharmaceutically acceptable salts. The preparation of salts and prodrugs can be carried out by methods known in the art. For example, metal salts can be prepared by reaction of a peptide of the invention with a metal hydroxide. An acid salt can be prepared by reacting an appropriate acid with a peptide of the invention.

The terms "selective" and "selectivity" as used herein refers to agents that modulate (e.g. activate) an ion channel subtype of interest without displaying substantial modulation of one or more other ion channel subtypes. Accordingly, an agent that is selective for $Na_v1.1$ exhibits $Na_v1.1$ selectivity of greater than about 2-fold, 5-fold, 10-fold, 20-fold, 50-fold or greater than about 100-fold with respect to modulation of one or more other $Na_v$ subtypes (i.e. one or more of $Na_v1.2$-1.9); preferably with respect to $Na_v1.2$ and $Na_v1.5$; more preferably with respect to $Na_v1.2$, $Na_v1.4$, $Na_v1.5$, $Na_v1.7$ and $Na_v1.8$; most preferably with respect to $Na_v1.2$, $Na_v1.4$, $Na_v1.5$, $Na_v1.6$, $Na_v1.7$ and $Na_v1.8$.

As used herein, the term "solvate" refers to a complex of variable stoichiometry formed by a solute, such as a peptide of the invention, and a solvent. Such solvents should not interfere with the biological activity of the solute.

The term "stringency" as used herein, refers to the temperature and ionic strength conditions, and presence or absence of certain organic solvents during hybridization and washing procedures. The higher the stringency, the higher will be the degree of complementarity between immobilized target nucleotide sequences and the labelled probe polynucleotide sequences that remain hybridized to the target after washing. The term "high stringency" refers to temperature and ionic conditions under which only nucleotide sequences having a high frequency of complementary bases will hybridize. The stringency required is nucleotide sequence dependent and depends upon the various components present during hybridization. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

The term "subject" as used herein refers to a vertebrate subject, particularly a mammalian or avian subject, for whom therapy or prophylaxis is desired. Suitable subjects include, but are not limited to, primates; avians; livestock animals such as sheep, cows, horses, deer, donkeys and pigs; laboratory test animals such as rabbits, mice, rats, guinea pigs and hamsters; companion animals such as cats and dogs; and captive wild animals such as foxes, deer and dingoes. In particular, the subject is a human. However, it will be understood that the aforementioned terms do not imply that symptoms are present.

2. Methods of $Na_v$ Modulation

The present invention relates to peptides that modulate $Na_v$ channels. In particular, the present invention relates to peptides that enhance $Na_v1.1$ activity. The peptides of the invention are useful in indications in which enhancing $Na_v1.1$ activity may be of benefit, for example, in epilepsy such as Dravet syndrome, generalised epilepsy with febrile seizures plus, borderline severe myoclonic epilepsy of infancy and intractable childhood epilepsy with generalised tonic-clonic seizures; Alzheimer's disease; autism spectrum disorders such as autism; and schizophrenia. The invention also relates to pharmaceutical compositions comprising these peptides.

In one aspect of the present invention, there is provided a method of enhancing $Na_v1.1$ activity, comprising contacting a $Na_v1.1$ expressing cell with an isolated, synthetic or recombinant peptide comprising, consisting or consisting essentially of SEQ ID NO: 1:

[SEQ ID NO: 1]
$Xaa_1CRYLFGGCXaa_2Xaa_3TXaa_4DCCKHLXaa_5CRXaa_6DXaa_7Xaa_8$
$YCZ_1$ wherein:
$Xaa_1$ is absent or is selected from acidic amino acid residues, including Asp and Glu;
$Xaa_2$ is selected from small amino acid residues, including Ser and Thr, and basic amino acid residues, including Arg, His and Lys;
$Xaa_3$ is selected from selected from small amino acid residues, including Ser and Thr;
$Xaa_4$ is selected from small amino acid residues, including Ser, Thr, Ala and Gly;
$Xaa_5$ is selected from small amino acid residues, including Ser, Thr, Ala and Gly;
$Xaa_6$ is selected from small amino acid residues, including Ser and Thr;
$Xaa_7$ is selected from aromatic amino acid residues, including Phe, Trp and Tyr, and hydrophobic amino acid residues, including Ile, Leu and Val;
$Xaa_8$ is selected from aromatic amino acid residues, including Phe, Trp and Tyr, and basic amino acid residues, including Arg, His and Lys; and
$Z_1$ is absent or is an amino acid sequence of SEQ ID NO: 2:

[SEQ ID NO: 2]
$AWDGTFXaa_9$ wherein:
$Xaa_9$ is absent or is a small amino acid residue, including Ser and Thr.

In some embodiments, $Xaa_1$ to $Xaa_8$ are selected from a combination of one or more of the following:
$Xaa_1$ is Glu;
$Xaa_2$ is Lys or Ser;
$Xaa_3$ is Ser or Thr;
$Xaa_4$ is Ala or Ser;
$Xaa_5$ is Gly or Ser;
$Xaa_6$ is Ser or Thr;
$Xaa_7$ is Leu or Trp; and
$Xaa_8$ is Lys or Tyr.

In some embodiments, $Xaa_9$ is Ser.

In a further embodiment, the isolated, synthetic or recombinant peptide useful in the invention comprises, consists or consists essentially of SEQ ID NO: 3:

[SEQ ID NO: 3]
$ECRYLFGGCXaa_{10}Xaa_{11}TXaa_{12}DCCKHLXaa_{13}CRXaa_{14}DXaa_{15}Xaa_{16}$
$YCAWDGTFXaa_{17}$ wherein:
$Xaa_{10}$ is selected from small amino acid residues, including Ser and Thr, and basic amino acid residues, including Arg, His and Lys;
$Xaa_{11}$ is selected from small amino acid residues, including Ser and Thr;
$Xaa_{12}$ is selected from small amino acid residues, including Ser, Thr, Ala and Gly;
$Xaa_{13}$ is selected from small amino acid residues, including Ser, Thr, Ala and Gly;
$Xaa_{14}$ is selected from small amino acid residues, including Ser and Thr;
$Xaa_{15}$ is selected from aromatic amino acid residues, including Phe, Trp and Tyr, and hydrophobic amino acid residues, including Ile, Leu and Val;

Xaa$_{16}$ is selected from aromatic amino acid residues, including Phe, Trp and Tyr, and basic amino acid residues, including Arg, His and Lys; and Xaa$_{17}$ is absent or is a small amino acid residue, including Ser and Thr.

In some embodiments, Xaa$_{10}$ to Xaa$_{17}$ are selected from a combination of one or more of the following:
Xaa$_{10}$ is Lys or Ser;
Xaa$_{11}$ is Ser or Thr;
Xaa$_{12}$ is Ala or Ser;
Xaa$_{13}$ is Ser or Gly;
Xaa$_{14}$ is Ser or Thr;
Xaa$_{15}$ is Trp or Leu;
Xaa$_{16}$ is Lys or Tyr; and
Xaa$_{17}$ is absent or Ser.

In some embodiments, the isolated, synthetic or recombinant peptide useful in the invention comprises, consists or consists essentially of:

[SEQ ID NO: 4]
ECRYLFGGCSSTSDCCKHLSCRSDWKYCAWDGTFS or

[SEQ ID NO: 5]
ECRYLFGGCKTTADCCKHLGCRTDLYYCAWDGTF.

The peptide of SEQ ID NO: 4 is designated as Hm1a and the peptide of SEQ ID NO: 5 is designated as Hm1b.

In particular embodiments, the isolated, synthetic or recombinant peptide useful in the invention comprises, consists or consists essentially of the amino acid sequence of SEQ ID NO: 5.

In some embodiments, the isolated, synthetic or recombinant peptide useful in the invention comprises, consists or consists essentially of:

[SEQ ID NO: 6]
ECRYLFGGCSTTADCCKHLGCRTDLYYCAWDGTF.

The amino acid sequence of the peptides useful in the invention is defined in terms of amino acids of certain characteristics or sub-classes. Amino acid residues are generally sub-classified into major sub-classes as follows:

Acidic: The residue has a negative charge due to loss of a proton at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with protons at physiological pH or within one or two pH units thereof (e.g. histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residue is charged at physiological pH and, therefore, includes amino acids having acidic or basic side chains, such as glutamic acid, aspartic acid, arginine, lysine and histidine.

Hydrophobic: The residue is not charged at physiological pH and the residue is repelled by aqueous solution so as to seek the inner positions in the conformation of a peptide in which it is contained when the peptide is in aqueous medium at physiological pH. Amino acids having a hydrophobic side chain include tyrosine, valine, isoleucine, leucine, methionine, phenylalanine and tryptophan.

Neutral/polar: The residues are not charged at physiological pH but the residue is not sufficiently repelled by aqueous solutions so that it would seek inner positions in the conformation of a peptide in which it is contained when the peptide is in aqueous medium at physiological pH. Amino acids having a neutral/polar side chain include asparagine, glutamine, cysteine, histidine, serine and threonine.

This description also characterises certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded amino acid proline (which formally is an imino acid) is a special case due to its known effects on the secondary structure of peptide chains. The structure of proline differs from all the other naturally-occurring amino acids in that its side chain is bonded to the nitrogen of the α-amino group, as well as the α-carbon. Several amino acid similarity matrices (e.g. PAM120 matrix and PAM250 matrix as disclosed for example by Dayhoff, et al. (1978) A model of evolutionary change in proteins. Matrices for determining distance relationships, in M. O. Dayhoff, (ed.), Atlas of protein sequence and structure, Vol. 5, pp. 345-358, National Biomedical Research Foundation, Washington D.C.; and by Gonnet, et al. (1992) *Science*, 256(5062): 1443-1445), however, include proline in the same group as glycine, serine, alanine and threonine. Accordingly, for the purposes of the present invention, proline is classified as a "small" amino acid.

The degree of attraction or repulsion required for classification as polar or non-polar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small amino acid residues are, of course, always non-aromatic. Dependent on their structural properties, amino acid residues may fall in two or more classes. For the naturally-occurring protein amino acids, sub-classification according to this scheme is presented in Table 1.

TABLE 1

Amino Acid Sub-Classification

| Sub-classes | Amino Acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Nonpolar/neutral | Alanine, Glycine, Isoleucine, Leucine, Methionine, Phenylalanine, Proline, Tryptophan, Valine |

TABLE 1-continued

Amino Acid Sub-Classification

| Sub-classes | Amino Acids |
|---|---|
| Polar/neutral | Asparagine, Histidine, Glutamine, Cysteine, Serine, Threonine, Tyrosine |
| Polar/negative | Aspartic acid, Glutamic acid |
| Polar/positive | Lysine, Arginine |
| Polar/large | Asparagine, Glutamine |
| Polar | Arginine, Asparagine, Aspartic acid, Cysteine, Glutamic acid, Glutamine, Histidine, Lysine, Serine, Threonine, Tyrosine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartic acid with a glutamic acid, a threonine with a serine, or a similar replacement of an amino acid with a structurally related amino acid will not have a major effect on the properties of the resulting variant peptide useful in the invention. Whether an amino acid change results in a peptide that enhances $Na_v1.1$ activity can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 2

| Exemplary and Preferred Amino Acid Substitutions | | |
|---|---|---|
| Original Residue | Exemplary Substitutions | Preferred Substitutions |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |

TABLE 2-continued

| Exemplary and Preferred Amino Acid Substitutions | | |
|---|---|---|
| Original Residue | Exemplary Substitutions | Preferred Substitutions |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, *Biochemistry*, third edition, Wm. C. Brown Publishers (1993).

Thus, a predicted non-essential amino acid residue in a peptide useful in the invention is typically replaced with another amino acid residue from the same side chain family. Alternatively, mutations can be introduced randomly along all or part of the coding sequence of a peptide useful in the invention, such as by saturation mutagenesis, and the resultant mutants can be screened for an activity of the parent polypeptide, as described for example herein, to identify mutants which retain that activity. Following mutagenesis of the coding sequences, the encoded peptide can be expressed recombinantly and its activity determined. A "non-essential" amino acid residue is a residue that can be altered from the wild-type sequence of an embodiment peptide useful in the invention without abolishing or substantially altering one or more of its activities. Suitably, the alteration does not substantially alter one of these activities, for example, the activity is at least 20%, 40%, 60%, 70% or 80% of that of the wild-type. By contrast, an "essential" amino acid residue is a residue that, when altered from the wild-type sequence of an embodiment peptide useful in the invention, results in abolition of an activity of the parent molecule such that less than 20% of the wild-type activity is present.

Accordingly, the present invention also contemplates variants of the Hm1a and Hm1b peptide sequences useful in the invention, wherein the variants are distinguished from the parent sequence by the addition, deletion, or substitution of one or more amino acid residues. In general, variants will display at least about 80%, 81%, 82%, 83%, 84%, 85%, 86%, 87%, 88%, 89%, 90%, 91%, 92%, 93%, 94%, 95%, 96%, 97%, 98%, 99% sequence similarity to a parent or reference peptide sequence as, for example, set forth in SEQ ID NO: 4 or 5, as determined by sequence alignment programs described elsewhere herein using default parameters. Desirably, variants will have at least 80%, 81%, 82%, 83%, 84%, 85%, 86%, 87%, 88%, 89%, 90%, 91%, 92%, 93%, 94%, 95%, 96%, 97%, 98%, 99% sequence identity to a parent or reference peptide sequence as, for example, set forth in SEQ ID NO: 4 or 5, as determined by sequence alignment programs described herein using default parameters. Variants of Hm1a and Hm1b, which fall within the scope of a variant peptide useful in the invention, may differ from the parent molecule generally by at least 1, but by less than 8, 7, 6, 5, 4, 3, 2 or 1 amino acid residue(s). In some embodiments, a variant peptide useful in the invention differs from the corresponding sequence in SEQ ID NO: 4 or 5 by at least 1, but by less than 8, 7, 6, 5, 4, 3, 2 or 1 amino acid residue(s). In some embodiments, the amino acid sequence of the variant peptide useful in the invention comprises at least six cysteine residues, preferably wherein the cysteine residues are located at positions 2, 9, 15, 16, 21 and 28 (numbered from the N-terminus of the corresponding linear peptide). In some embodiments, the amino acid sequence of the variant peptide useful in the invention comprises Glu at position 1, Arg at position 3, Tyr at position 4, Leu at position 5, Phe at position 6, Gly at position 7, Gly at position 8, Thr at position 12, Asp at position 14, Lys at position 17, His at position 18, Leu at position 19, Arg at position 22, Asp at position 24, Tyr at position 27, Ala at position 29, Trp at position 30, Asp at position 31, Gly at position 32, Thr at position 33 and/or Phe at position 34 (numbered from the N-terminus). In some embodiments, the amino acid sequence of the variant peptide useful in the invention comprises SEQ ID NO: 1 and/or 3. In particular embodiments, the variant peptide useful in the invention enhances $Na_v1.1$ activity.

If the sequence comparison requires alignment, the sequences are typically aligned for maximum similarity or identity. "Looped" out sequences from deletions or insertions, or mismatches, are generally considered differences. The differences are, suitably, differences or changes at a non-essential residue or a conservative substitution.

In some embodiments, calculations of sequence similarity or sequence identity between sequences are performed as follows:

To determine the percent identity of two amino acid sequences or of two nucleic acid sequences, the sequences are aligned for optimal comparison purposes (e.g. gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 40%, more usually at least 50% or 60%, and even more usually at least 70%, 80%, 90% or 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e. conservative substitution) at the corresponding position in the second sequence, then the molecules are similar at that position.

The percent identity between the two sequences is a function of the number of identical amino acid residues shared by the sequences at individual positions, taking into account the number of gaps and the length of each gap, which need to be introduced for optimal alignment of the two sequences. By contrast, the percent similarity between the two sequences is a function of the number of identical and similar amino acid residues shared by the sequences at individual positions, taking into account the number of gaps and the length of each gap, which need to be introduced for optimal alignment of the two sequences.

The comparison of sequences and determination of percent identity or percent similarity between sequences can be accomplished using a mathematical algorithm. In certain embodiments, the percent identity or similarity between amino acid sequences is determined using the Needleman and Wnnsch, (1970, *J. Mol. Biol.*, 48: 444-453) algorithm which has been incorporated into the GAP program in the GCG software package (Devereaux, et al. (1984) *Nucleic Acids Research*, 12: 387-395), using either a Blosum 62 matrix or a PAM250 matrix, and a gap weight of 16, 14, 12, 10, 8, 6, or 4 and a length weight of 1, 2, 3, 4, 5, or 6. In some embodiments, the percent identity or similarity between amino acid sequences can be determined using the algorithm of Meyers and Miller (1989, *Cabios*, 4: 11-17) which has been incorporated into the ALIGN program (version 2.0), using a PAM120 weight residue table, a gap length penalty of 12 and a gap penalty of 4.

The present invention also contemplates an isolated, synthetic or recombinant peptide useful in the invention that is encoded by a polynucleotide sequence that hybridizes under stringency conditions as defined herein, especially under medium, high or very high stringency conditions, preferably under high or very high stringency conditions, to a polynucleotide sequence encoding the peptides of SEQ ID NO: 1, 3, 4 and/or 5 or the non-coding strand thereof. The invention also contemplates an isolated nucleic acid molecule comprising a polynucleotide sequence that hybridizes under stringency conditions as defined herein, especially under medium, high or very high stringency conditions, preferably under high or very high stringency conditions, to a polynucleotide sequence encoding the peptides of SEQ ID NO: 1, 3, 4 and/or 5 or the non-coding strand thereof.

As used herein, the term "hybridizes under stringency conditions" describes conditions for hybridization and washing and may encompass low stringency, medium stringency, high stringency and very high stringency conditions. Guidance for performing hybridization reactions can be found in Ausubel, et al. (1998) Current Protocols in Molecular Biology (John Wiley and Sons, Inc.), in particular sections 6.3.1-6.3.6. Both aqueous and non-aqueous methods can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% sodium dodecyl sulfate (SDS) for hybridization at 65° C., and (i) 2× sodium chloride/sodium citrate (SSC), 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6×SSC at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In some aspects of the present invention, there is provided an isolated, synthetic or recombinant peptide useful in the invention that is encoded by a polynucleotide sequence that hybridizes under high stringency conditions to a polynucleotide sequence encoding the peptides of SEQ ID NO: 1, 3, 4 and/or 5 or the non-coding strand thereof. In certain embodiments, the isolated, synthetic or recombinant peptide useful in the invention is encoded by a polynucleotide sequence that hybridizes under very high stringency conditions to a polynucleotide sequence encoding the peptides of SEQ ID NO: 1, 3, 4 and/or 5 or the non-coding strand thereof. One embodiment of very high stringency conditions includes hybridizing 0.5 M sodium phosphate, 7% SDS at 65° C., followed by one or more washes at 0.2×SSC, 1% SDS at 65° C. In some embodiments, the amino acid sequence of the isolated, synthetic or recombinant peptide useful in the invention comprises at least six cysteine residues, preferably wherein the cysteine residues are located at positions 2, 9, 15, 16, 21 and 28 (numbered from the N-terminus of the corresponding linear peptide). In some embodiments, the amino acid sequence comprises Glu at position 1, Arg at position 3, Tyr at position 4, Leu at position 5, Phe at position 6, Gly at position 7, Gly at position 8, Thr at position 12, Asp at position 14, Lys at position 17, His at position 18, Leu at position 19, Arg at position 22, Asp at position 24, Tyr at position 27, Ala at position 29, Trp at position 30, Asp at position 31, Gly at position 32, Thr at position 33 and/or Phe at position 34 (numbered from the N-terminus). In some embodiments, the amino acid sequence comprises SEQ ID NO: 1 and/or 3. In particular embodiments, the peptide useful in the invention enhances Na$_v$1.1 activity.

Other stringency conditions are well known in the art and a person skilled in the art will recognize that various factors can be manipulated to optimize the specificity of the hybridization. Optimization of the stringency of the final washes can serve to ensure a high degree of hybridization. For detailed examples, see Ausubel, et al. (1998) Current Protocols in Molecular Biology (John Wiley and Sons, Inc.), in particular pages 2.10.1 to 2.10.16 and Sambrook, et al. (1989) Molecular Cloning: A Laboratory Manual (Cold Spring Harbour Press), in particular Sections 1.101 to 1.104.

While stringent washes are typically carried out at temperatures from about 42° C. to 68° C., a person skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel, et al. (1998) Current Protocols in Molecular Biology (John Wiley and Sons, Inc.) at page 2.10.8). In general, the $T_m$ of a perfectly matched duplex of DNA may be predicted as an approximation by the formula:

$$T_m = 81.5 + 16.6\ (\log_{10} M) + 0.41\ (\%\ G+C) - 0.63\ (\%\ \text{formamide}) - (600/\text{length})$$

wherein: M is the concentration of Na$^+$, preferably in the range of 0.01 M to 0.4 M; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$—15° C. for high stringency, or $T_m$—30° C. for moderate stringency.

In one example of a hybridization procedure, a membrane (e.g. a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrrolidone and 0.1% BSA), 0.1% SDS and 200 mg/mL denatured salmon sperm DNA) containing labeled probe. The membrane is then subjected to two sequential medium stringency washes (i.e. 2×SSC, 0.1% SDS for 15 min at 45° C., followed by 2×SSC, 0.1% SDS for 15 min at 50° C.), followed by two sequential higher stringency washes (i.e. 0.2×SSC, 0.1% SDS for 12 min at 55° C. followed by 0.2×SSC and 0.1% SDS solution for 12 min at 65-68° C.

The peptides useful in the present invention also encompass peptides comprising amino acids with modified side chains, incorporation of unnatural amino acid residues and/or their derivatives during peptide synthesis and the use of cross-linkers and other methods which impose conformational constraints on the peptides of the invention. Examples of side chain modifications include modifications of amino groups, such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with sodium borohydride; reductive alkylation by reaction with an aldehyde followed by reduction with sodium borohydride; substitution of disulfide bonds with diselenide bonds by replacing cysteine residues with selenocysteine residues; and trinitrobenzylation of amino groups with 2,4,6-trinitrobenzene sulfonic acid (TNBS).

The carboxyl group may be modified by carbodiimide activation through O-acylisourea formation followed by subsequent derivitisation, for example, to a corresponding amide.

The guanidine group of arginine residues may be modified by formation of heterocyclic condensation products with reagents such as 2,3-butanedione, phenylglyoxal and glyoxal.

Tryptophan residues may be modified, for example, by alkylation of the indole ring with 2-hydroxy-5-nitrobenzyl bromide or sulfonyl halides, or by oxidation with N-bromosuccinimide.

Tyrosine residues may be modified by nitration with tetranitromethane to form 3-nitrotyrosine derivatives.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include, but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine, selenocysteine and/or D-isomers of amino acids. A list of unnatural amino acids contemplated by the present invention is shown in Table 3.

TABLE 3

Exemplary Unnatural Amino Acids
Non-Conventional Amino Acids

| | |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-methylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-naphthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvaline | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | L-selenocysteine |
| D-selenocysteine | |

The peptides useful in the present invention, particularly the peptides of SEQ ID NO: 1, 3, 4 and 5, have at least six cysteine residues. Preferably, the peptides have six cysteine residues. The cysteine residues may be bonded in pairs through disulfide bonds. In one embodiment, the peptides useful in the present invention, particularly the peptides of SEQ ID NO: 1, 3, 4 and 5, possess six cysteine residues bonded in pairs to form three disulfide bonds.

A large proportion of spider venom peptides comprising six cysteine residues have a cysteine connectivity between cysteine residues I and IV, II and V, and III and VI (numbered from the N-terminus of the corresponding linear peptide). Preferably, this disulfide connectivity is present in the peptides useful in the present invention, especially the peptides of SEQ ID NO: 1, 3, 4 and 5. In some embodiments, the peptides useful in the invention, especially the peptides of SEQ ID NO:1, 3, 4 and 5, comprise disulfide bonds formed between the side chains of Cys 2 and Cys 16, Cys 9 and Cys 21, and Cys 15 and Cys 28 (numbered from the N-terminus of the corresponding linear peptide).

Without wishing to be bound by theory, this disulfide bond connectivity forms an inhibitor cystine knot motif in which a ring formed by two of the disulfide bonds and the intervening sections of the peptide backbone is pierced by the third disulfide bond. Peptides comprising an inhibitor cystine knot motif have high levels of chemical and thermal stability, as well as resistance to proteases, which may be advantageous for therapeutic use.

Peptides comprising an inhibitor cystine knot motif possess at least four loops formed by at least three disulfide bonds. Each loop comprises a peptide backbone with a varied number of amino acids. For example, the peptide backbone between Cys I and II (loop 1) may comprise about 2 to about 7 amino acid residues, the peptide backbone between Cys II and Cys III (loop 2) may comprise about 3 to about 11 amino acid residues, the peptide backbone between Cys III and Cys IV (loop 3) may comprise about 0 to about 7 amino acid residues, the peptide backbone between Cys IV and Cys V (loop 4) may comprise about 1 to about 17 amino acid residues and the peptide backbone between Cys V and Cys VI (loop 5) may comprise about 1 to about 19 amino acid residues. Accordingly, the present invention also contemplates variant peptides useful in the invention that differ from the amino acid sequence of SEQ ID NO: 1, 3, 4 or 5 by the insertion of one or more amino acid residues in any one of loops 1 to 5. In some embodiments, the variant peptide useful in the invention comprises the insertion of 1 or 2 amino acid residues between Cys 2 and Cys 9; the insertion of 1, 2, 3, 4, 5 or 6 amino acid residues between Cys 9 and Cys 15; the insertion of 1, 2, 3, 4, 5, 6 or 7 amino acid residues between Cys 15 and Cys 16; the insertion of 1, 2, 3, 4, 5, 6, 7 or 8 amino acid residues between Cys 16 and Cys 21; and/or the insertion of 1, 2, 3, 4, 5, 6, 7 or 8 amino acid residues between Cys 21 and Cys 28; wherein the amino acid residues may be selected from any amino acid residue and are inserted at any position in the amino acid sequence between the two designated cysteine residues (numbered from the N-terminus of the corresponding linear peptide).

In some embodiments, one or more of the disulfide bonds of the peptides useful in the invention are replaced with a suitable alternative, such as a diselenide bond, a lanthionine bond, a lactam bond or a dimethylene bond. In particular embodiments, at least two cysteine residues are substituted with selenocysteine residues. The selenocysteine residues in the sequences must be positioned such that when the peptide is oxidised, a diselenide bond is produced between the side chains of two selenocysteine residues.

Additional amino acids or other substituents may be added to the N- or C-termini, if present, of the peptides useful in the present invention, for example 1, 2, 3, 4 or 5 amino acid residues. For example, the peptides useful in the present invention may form part of a longer sequence with additional amino acids added to either or both of the N- and C-termini.

In some embodiments, the peptides useful in the present invention comprise a stabilising moiety. The stabilising moiety may be conjugated at any point on the peptide. Suitable stabilising moieties include polyethylene glycol (PEG) or a capping moiety, including an acetyl group, pyroglutamate, pyroglutamic acid, or an amino group. In preferred embodiments, the acetyl group, pyroglutamate and/or pyroglutamic acid are conjugated to the N-terminal amino acid residue of the peptide, if present. In particular embodiments, the N-terminus of the peptide, if present, is a pyroglutamide or acetamide. In preferred embodiments, the amino group is conjugated to the C-terminal amino acid residue of the peptide, if present. In particular embodiments, the peptide has a primary amide at the C-terminus. In preferred embodiments, the PEG is conjugated to the N-terminal or C-terminal amino acid residue of the peptide, if present, or through the amine of a lysine side-chain, especially through the N-terminal amino acid residue or through the amine of a lysine side-chain.

In preferred embodiments, the peptides useful in the present invention have a primary amide or a free carboxyl group at the C-terminus and a primary amine at the N-terminus, if N- and C-termini are present.

In some embodiments, the peptides useful in the present invention comprise a membrane permeating moiety. The membrane permeating moiety may be conjugated at any point on the peptide. In preferred embodiments, the membrane permeating moiety is a lipid moiety, such as a $C_{10}$-$C_{20}$ fatty acyl group, especially hexadecanoyl (palmitoyl; $C_{16}$) or tetradecanoyl (myristoyl; $C_{14}$); most especially tetradecanoyl. In preferred embodiments, the membrane permeating moiety is conjugated to the N- or C-terminal amino acid residue, if present, or through the amine of a lysine side-chain of the peptide, especially the N-terminal amino acid residue of the peptide or through the amine of a lysine side-chain.

In some embodiments, the peptides useful in the present invention are cyclic peptides. Without wishing to be bound by theory, cyclisation of peptides is thought to decrease the susceptibility of the peptides to degradation. In particular embodiments, the peptides are cyclised using N-to-C cyclisation (head to tail cyclisation), preferably through an amide bond. Such peptides do not possess N- or C-terminal amino acid residues. In particular embodiments, the peptides have an amide-cyclised peptide backbone. In other embodiments, the peptides are cyclised using side-chain to side-chain cyclisation, preferably through a disulfide bond or a lactam bridge.

In some embodiments, the N- and C-termini are linked using a linking moiety. The linking moiety may be a peptide linker such that cyclisation produces an amide-cyclised peptide backbone. Variation within the peptide sequence of the linking moiety is possible, such that the linking moiety may be modified to alter the physicochemical properties of the peptides and potentially reduce side effects of the peptides of the invention or otherwise improve the therapeutic use of the peptides, for example, by improving stability. The linking moiety will be of suitable length to span the distance between the N- and C-termini of the peptide without substantially altering the structural conformation of the peptide, for example, a peptidic linking moiety may be between 2 and 10 amino acid residues in length. In some embodiments, longer or shorter peptidic linking moieties may be required.

The peptides useful in the present invention may be in the form of salts or prodrugs. The salts of the peptides useful in the present invention are preferably pharmaceutically acceptable, but it will be appreciated that non-pharmaceutically acceptable salts also fall within the scope of the present invention.

The peptides useful in the present invention may be in crystalline form and/or in the form of solvates, for example, hydrates. Solvation may be performed using methods known in the art.

In some embodiments, the peptides useful in the invention selectively enhance $Na_v1.1$ activity over at least one other subtype of voltage-gated sodium channel, particularly $Na_v1.2$ and $Na_v1.5$. In some embodiments, the peptides useful in the invention exhibit $Na_v1.1$ selectivity of greater than about 2-fold, 5-fold, 10-fold, 20-fold, 50-fold or greater than about 100-fold with respect to enhancing activity of one or more other $Na_v$ subtypes (i.e. one or more of $Na_v1.2$-$Na_v1.9$); preferably with respect to $Na_v1.2$ and $Na_v1.5$; more preferably with respect to $Na_v1.2$, $Na_v1.4$, $Na_v1.5$, $Na_v1.7$ and $Na_v1.8$; most preferably with respect to $Na_v1.2$, $Na_v1.4$, $Na_v1.5$, $Na_v1.6$, $Na_v1.7$ and $Na_v1.8$.

In another aspect of the present invention, there is provided a method of treating or preventing a condition in respect of which enhancing $Na_v1.1$ activity is associated with effective treatment, comprising administration of an isolated, synthetic or recombinant peptide comprising, consisting or consisting essentially of SEQ ID NO: 1, 3, 4 or 5 or variant peptide described herein. In particular embodiments, the peptide is administered to a subject in need of such treatment, although the peptide may be administered prophylactically. In particular embodiments, the subject is a mammal, especially a human.

The present invention also provides the use of an isolated, synthetic or recombinant peptide comprising, consisting or consisting essentially of SEQ ID NO: 1, 3, 4 or 5 or variant peptide described herein in the manufacture of a medicament for the treatment or prevention of a condition in respect of which enhancing $Na_v1.1$ activity is associated with effective treatment.

The conditions in which enhancing $Na_v1.1$ activity is associated with effective treatment may include, but are not limited to, epilepsy such as Dravet syndrome, generalised epilepsy with febrile seizures plus, borderline severe myoclonic epilepsy of infancy and intractable childhood epilepsy with generalised tonic-clonic seizures; Alzheimer's disease; autism spectrum disorders such as autism; and schizophrenia.

In some embodiments, the isolated, synthetic or recombinant peptide comprising, consisting or consisting essentially of SEQ ID NO: 1, 3, 4 or 5 or variant peptide described herein may be used for the treatment or prevention of epilepsy; preferably Dravet syndrome, generalised epilepsy with febrile seizures plus, borderline severe myoclonic epilepsy of infancy and intractable childhood epilepsy with generalised tonic-clonic seizures; especially Dravet syndrome.

In some embodiments, the isolated, synthetic or recombinant peptide comprising, consisting or consisting essentially of SEQ ID NO: 1, 3, 4 or 5 or variant peptide described herein may be used for the treatment or prevention of Alzheimer's disease.

In a further aspect of the present invention, there is provided a method of treating or preventing a condition characterised by reduced $Na_v1.1$ activity comprising administration of an isolated, synthetic or recombinant peptide comprising, consisting or consisting essentially of SEQ ID NO: 1, 3, 4 or 5 or variant peptide described herein.

Numerous epileptic conditions, such as Dravet syndrome, are characterised by mutations in the SCN1A gene, which encodes the pore-forming α-subunit of $Na_v1.1$. Approximately 85% of Dravet syndrome cases result from heterozygous loss of function mutations in the SCN1A gene caused by nonsense and missense variations. In the brain, $Na_v1.1$ is expressed predominantly in the axon initial segments of fast-spiking inhibitory interneurons. Without wishing to be bound by theory, it is thought that enhancing $Na_v1.1$ activity using the peptides of the invention will elevate Na$_v$1.1 activity in inhibitory interneurons.

In another aspect of the present invention, there is provided a method of treating or preventing a condition characterised by at least one loss of function mutation in SCN1A, comprising administration of an isolated, synthetic or recombinant peptide comprising, consisting or consisting essentially of SEQ ID NO: 1, 3, 4 or 5 or variant peptide described herein. The present invention also provides the use of an isolated, synthetic or recombinant peptide comprising, consisting or consisting essentially of SEQ ID NO: 1, 3, 4 or 5 or variant peptide described herein in the manufacture of a medicament for the treatment or prevention of a condition characterised by at least one loss of function mutation in SCN1A.

While the peptide useful in the invention may be the sole active ingredient administered to the subject, the administration of other active ingredients with said peptide is within the scope of the invention. For example, the isolated, synthetic or recombinant peptide comprising, consisting or consisting essentially of SEQ ID NO: 1, 3, 4 or 5 or variant peptide described herein may be administered with one or more therapeutic agents, such as other agents that enhance Na$_v$1.1 activity or some anticonvulsant drugs. Suitable therapeutic agents include, but are not limited to, benzodiazepines such as clobazam and clonazepam, stiripentol, valproic acid and salts thereof, topiramate and levetiracetam.

In another aspect of the present invention, there is provided a method of treating or preventing epilepsy, comprising administration of an isolated, synthetic or recombinant peptide comprising, consisting or consisting essentially of SEQ ID NO: 1, 3, 4 or 5 or variant peptide described herein in combination with an anticonvulsant compound. Suitable anticonvulsant compounds include, but are not limited to, benzodiazepines such as clobazam and clonazepam, stiripentol, valproic acid and salts thereof, topiramate and levetiracetam.

The peptide useful in the present invention may be administered by an appropriate route including, but not limited to, intranasal, inhalation, intravenous, intracerebroventricular, intramuscular, intraperitoneal, subcutaneous, intracerebral, intrathecal and epidural administration; particularly intrathecal, intranasal and inhalation administration.

A skilled person would be well aware of suitable assays used to assess Na$_v$1.1 activity and to identify peptides that enhance Na$_v$1.1 activity, for example, the assays described in Jeffrey, et al. (2006) Expression and Analysis of Recombinant Ion Channels (WILEY-VCH Verlag GmbH & Co. KgaA), particularly Chapter 1; Kaczorowski, et al. (2011) *Frontiers in Pharmacology*, 2(78): 1-11; Jensen, et al. (2014) *Trends in Pharmacological Sciences*, 35(3): 113-118; Felix, et al. (2004) *Assay Drug Dev Technol*, 2: 260-268; and Kaczorowski, et al. (2008) *J Gen Physiol*, 131(5): 399-405.

3. Peptides that Modulate Na$_v$1.1

In another aspect of the present invention, there is provided an isolated, synthetic or recombinant peptide comprising, consisting or consisting essentially of SEQ ID NO: 1:

[SEQ ID NO: 1]
Xaa$_1$CRYLFGGCXaa$_2$Xaa$_3$TXaa$_4$DCCKHLXaa$_5$CRXaa$_6$DXaa$_7$Xaa$_8$YCZ$_1$ wherein:

Xaa$_1$ is absent or is selected from acidic amino acid residues, including Asp and Glu;

Xaa$_2$ is selected from small amino acid residues, including Ser and Thr, and basic amino acid residues, including Arg, His and Lys;

Xaa$_3$ is selected from selected from small amino acid residues, including Ser and Thr;

Xaa$_4$ is selected from small amino acid residues, including Ser, Thr, Ala and Gly;

Xaa$_5$ is selected from small amino acid residues, including Ser, Thr, Ala and Gly;

Xaa$_6$ is selected from small amino acid residues, including Ser and Thr;

Xaa$_7$ is selected from aromatic amino acid residues, including Phe, Trp and Tyr, and hydrophobic amino acid residues, including Ile, Leu and Val;

Xaa$_8$ is selected from aromatic amino acid residues, including Phe, Trp and Tyr, and basic amino acid residues, including Arg, His and Lys;

Z$_1$ is absent or is an amino acid sequence of SEQ ID NO: 2:

[SEQ ID NO: 2]
AWDGTFXaa$_9$ wherein:

Xaa$_9$ is absent or is a small amino acid residue, including Ser and Thr; and wherein the peptide is other than a peptide consisting of the amino acid sequence of SEQ ID NO: 4:

[SEQ ID NO: 4]
ECRYLFGGCSSTSDCCKHLSCRSDWKYCAWDGTFS.

In some embodiments, Xaa$_1$ to Xaa$_8$ are selected from a combination of one or more of the following:

Xaa$_1$ is Glu;

Xaa$_2$ is Lys or Ser;

Xaa$_3$ is Ser or Thr;

Xaa$_4$ is Ala or Ser;

Xaa$_5$ is Gly or Ser;

Xaa$_6$ is Ser or Thr;

Xaa$_7$ is Leu or Trp; and

Xaa$_8$ is Lys or Tyr.

In some embodiments, Xaa$_9$ is Ser.

In a further embodiment, the isolated, synthetic or recombinant peptide comprises, consists or consists essentially of SEQ ID NO: 3:

[SEQ ID NO: 3]
ECRYLFGGCXaa$_{10}$Xaa$_{11}$TXaa$_{12}$DCCKHLXaa$_{13}$CRXaa$_{14}$DXaa$_{15}$Xaa$_{16}$YCAWDGTFXaa$_{17}$ wherein:

Xaa$_{10}$ is selected from small amino acid residues, including Ser and Thr, and basic amino acid residues, including Arg, His and Lys;

Xaa$_{11}$ is selected from small amino acid residues, including Ser and Thr;

Xaa$_{12}$ is selected from small amino acid residues, including Ser, Thr, Ala and Gly;

Xaa$_{13}$ is selected from small amino acid residues, including Ser, Thr, Ala and Gly;

$Xaa_{14}$ is selected from small amino acid residues, including Ser and Thr;

$Xaa_{15}$ is selected from aromatic amino acid residues, including Phe, Trp and Tyr, and hydrophobic amino acid residues, including Ile, Leu and Val;

$Xaa_{16}$ is selected from aromatic amino acid residues, including Phe, Trp and Tyr, and basic amino acid residues, including Arg, His and Lys; and $Xaa_{17}$ is absent or is a small amino acid residue, including Ser and Thr; and wherein the peptide is other than a peptide consisting of the amino acid sequence of SEQ ID NO: 4:

```
                                        [SEQ ID NO: 4]
ECRYLFGGCSSTSDCCKHLSCRSDWKYCAWDGTFS.
```

In some embodiments, $Xaa_{10}$ to $Xaa_{17}$ are selected from a combination of one or more of the following:

$Xaa_{10}$ is Ser or Lys;

$Xaa_{11}$ is Ser or Thr;

$Xaa_{12}$ is Ser or Ala;

$Xaa_{13}$ is Ser or Gly;

$Xaa_{14}$ is Ser or Thr;

$Xaa_{15}$ is Trp or Leu;

$Xaa_{16}$ is Lys or Tyr; and $Xaa_{17}$ is absent or Ser.

In some embodiments, the isolated, synthetic or recombinant peptide comprises, consists or consists essentially of SEQ ID NO: 5:

```
                                        [SEQ ID NO: 5]
ECRYLFGGCKTTADCCKHLGCRTDLYYCAWDGTF.
```

In some embodiments, the isolated, synthetic or recombinant peptide comprises, consists or consists essentially of SEQ ID NO: 6:

```
                                        [SEQ ID NO: 6]
ECRYLFGGCSTTADCCKHLGCRTDLYYCAWDGTF.
```

Further variants and embodiments of the peptides of the invention are as previously described herein.

In a further aspect of the present invention, there is provided an isolated nucleic acid molecule comprising a polynucleotide sequence that encodes the peptide of the invention or is complementary to a polynucleotide sequence that encodes a peptide of the invention.

The isolated nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules are typically isolated, in some embodiments, the nucleic acid molecules may be integrated into or ligated to or otherwise fused or associated with other genetic molecules, such as an expression vector. Generally, an expression vector includes transcriptional and translational regulatory nucleic acid operably linked to the polynucleotide sequence.

In a further aspect of the present invention, there is provided a genetic construct for expressing the nucleic acid molecules. Such constructs typically comprise a nucleic acid molecule as described above operably linked to a regulatory sequence.

The peptides of the present invention may be prepared using recombinant DNA techniques or by chemical synthesis.

In some embodiments, the peptides of the present invention are prepared using standard peptide synthesis methods, such as solution synthesis or solid phase synthesis, followed by oxidative disulfide bond formation. The chemical synthesis of the peptides of the invention may be performed manually or using an automated synthesiser. For example, the linear peptides may be synthesised using solid phase peptide synthesis using either Boc or Fmoc chemistry, as described in Merrifield (1963) *J Am Chem Soc*, 85(14): 2149-2154; Schnolzer, et al. (1992) *Int J Pept Protein Res*, 40: 180-193 and Cardosa, et al. (2015)*Mol Pharmacol*, 88(2): 291-303. Following deprotection and cleavage from the solid support, the linear peptides are purified using suitable methods, such as preparative chromatography. The purified linear peptides are then oxidised in buffered systems to form the disulfide bonds, followed by purification using a suitable means, such as preparative chromatography. Alternatively, a synthetic method involving selective disulfide bond formation may be used as described in, for example, Kent, et al. (1998) *Biopolymers*, 46: 53-63.

In other embodiments, the peptide may be cyclised. Cyclisation may be performed using several techniques, as described in Davies (2003) *J Pept Sci*, 9: 471-501. In particular embodiments, the linear peptide is synthesised using solid phase peptide synthesis involving Boc-chemistry, starting with a cysteine residue at the N-terminus and ending with a thioester at the C-terminus. Following deprotection and cleavage from the resin, the peptide is cyclised via a thiolactone intermediate, which subsequently rearranges to an amine-cyclised peptide. The reduced peptide is then oxidised to form the disulfide bonds.

Disulfide bond replacement with diselenide, lanthionine, lactam or dimethylene bonds may be prepared using methods known in the art, for example, as described in Muttenthaler and Alewood (2008) *J Pept Sci*, 14(12): 1223-1239; Li, et al. (2002) *Current Organic Chemistry*, 6: 411-440; and Fazio, et al. (2005) *Biopolymers (Peptide Science)*, 84(2): 205-218.

In some embodiments, the peptides of the present invention are prepared using recombinant DNA techniques. For example, the peptides of the invention may be prepared by a procedure including the steps of: (a) preparing a construct comprising a polynucleotide sequence that encodes the peptide of the invention and that is operably linked to a regulatory element; (b) introducing the construct into a host cell; (c) culturing the host cell to express the polynucleotide sequence to thereby produce the encoded peptide of the invention; and (d) isolating the peptide of the invention from the host cell. The peptide of the present invention may be prepared recombinantly using standard protocols, for example, as described in Klint, et al. (2013) *PLOS One*, 8(5): e63865; Sambrook, et al. (1989) Molecular Cloning: A Laboratory Manual (Cold Spring Harbour Press), in particular Sections 16 and 17; Ausubel, et al. (1998) Current Protocols in Molecular Biology (John Wiley and Sons, Inc.), in particular Chapters 10 and 16; and Coligan, et al. (1997) Current Protocols in Protein Science (John Wiley and Sons, Inc.), in particular Chapters 1, 5 and 6. When prepared under these conditions, the peptide may comprise one or more additional amino acid residues at the N-terminus, for example, Ser or Gly. Exemplary peptides include a peptide comprising, consisting or consisting essentially of:

SECRYLFGGCSSTSDCCKHLSCRSDWKYCAWDGTFS;   [SEQ ID NO: 7]

SECRYLFGGCKTTADCCKHLGCRTDLYYCAWDGTF;   [SEQ ID NO: 8]
or

SECRYLFGGCSTTADCCKHLGCRTDLYYCAWDGTF.   [SEQ ID NO: 9]

Under some circumstances it may be desirable to undertake oxidative bond formation of the expressed peptide after peptide expression. This may be preceded by a reductive step to provide the linear peptide. Suitable conditions for reduction and oxidation of the peptide will be readily determined by a person skilled in the art.

In some embodiments, the peptides of the present invention may be in the form of a pharmaceutical composition, wherein the pharmaceutical composition comprises a peptide of the invention and a pharmaceutically acceptable carrier or diluent.

The peptides of the invention may be formulated into the pharmaceutical compositions as neutral or salt forms.

As will be appreciated by those skilled in the art, the route of administration and the nature of the pharmaceutically acceptable carrier will depend on the nature of the condition and the subject to be treated. The particular carrier or delivery system and route of administration may be readily determined by a person skilled in the art. The carrier or delivery system and route of administration should be carefully selected to ensure that the activity of the peptide is not depleted during preparation of the formulation and the peptide is able to reach the site of action intact. The pharmaceutical compositions of the present invention may be administered through a variety of routes, including, but not limited to, intravenous, intramuscular, intraperitoneal, subcutaneous, intracerebral, intracerebroventricular, intrathecal, epidural, intranasal and inhalation administration; especially intrathecal, intranasal and inhalation administration.

The pharmaceutical forms suitable for injectable use include sterile injectable solutions or dispersions and sterile powders for the preparation of sterile injectable solutions. The pharmaceutical forms suitable for intranasal or inhalation delivery include solutions, dry powders, suspensions or emulsions. Such forms should be stable under the conditions of manufacture and storage and may be preserved against reduction, oxidation and microbial contamination.

A person skilled in the art will readily be able to determine appropriate formulations for the peptides of the present invention using conventional approaches. Identification of preferred pH ranges and suitable excipients, such as antioxidants, is routine in the art, for example, as described in Katdare and Chaubel (2006) Excipient Development for Pharmaceutical, Biotechnology and Drug Delivery Systems (CRC Press). Buffer systems are routinely used to provide pH values of a desired range and may include, but are not limited to, carboxylic acid buffers, such as acetate, citrate, lactate, tartrate and succinate; glycine; histidine; phosphate; tris(hydroxymethyl)aminomethane (Tris); arginine; sodium hydroxide; glutamate; and carbonate buffers. Suitable antioxidants may include, but are not limited to, phenolic compounds such as butylated hydroxytoluene (BHT) and butylated hydroxyanisole; vitamin E; ascorbic acid; reducing agents such as methionine or sulphite; metal chelators such as ethylene diamine tetraacetic acid (EDTA); cysteine hydrochloride; sodium bisulfite; sodium metabisulfite; sodium sulphite; ascorbyl palmitate; lecithin; propyl gallate; and alpha-tocopherol.

The solvent or dispersion medium may contain any of the conventional solvent or carrier systems for peptide actives and may contain, but is not limited to, water; ethanol; polyols, such as glycerol, propylene glycol and polyethylene glycol; vegetable oils; dimethylacetamide; N-methyl-2-pyrrolidone; dimethylsulfoxide; and combinations thereof.

The pharmaceutical compositions of the present invention may comprise, but are not limited to, preservatives including parabens, chlorobutanol, phenol, sorbic acid, thiomersal, benzalkonium chloride, phenyl ethyl alcohol, EDTA, chlorobutanol, phenol, benzyl alcohol and combinations thereof; agents that prolong absorption such as aluminium monostearate and gelatine; solubilising agents such as ethylene diamine dihydrochloride and polyvinylpyrrolidone; humectants such as sorbitol, glycerol and mannitol; mucoadhesive agents such as polyacrylic acids, xanthan gum, carboxymethylcellulose, hydroxypropylcellulose, hydroxypropylmethylcellulose, carrageenan, alginates and chitosan; viscosity modifiers such as propylene glycol, polyethylene glycol and glycerol; surfactants such as oleic acid, polysorbates, Tween, polyvinylpyrrolidone, lecithin and sorbitane trioleate; stabilising agents such as albumin, leucine, sugars e.g. sucrose, lactose, trehalose, dextrose and raffinose, and polyols such as mannitol and sorbitol; antiadherants such as magnesium stearate; and osmolality adjusting agents such as sugar and sodium chloride. In some embodiments, the pharmaceutical composition is isotonic with blood.

Injectable pharmaceutical forms may be delivered by any appropriate route, including intravenous, intramuscular, intraperitoneal, subcutaneous, intracerebral, intracerebroventricular, intrathecal and epidural injection or infusion; particularly intrathecal and intravenous injection or infusion; especially intrathecal injection or infusion. In some embodiments, the pharmaceutical composition is formulated for intrathecal administration.

Intranasal formulations may be administered in the form of a spray, drop or syringe; especially a spray.

Inhalation formulations may be administered in the form of an aerosol spray from a pressurised dispenser or container, which contains a propellant such as carbon dioxide gas, dichlorodifluoromethane, nitrogen, propane, hydrofluoroalkane or other suitable gas or combination of gases; or using a nebuliser.

The peptide of the invention may be incorporated into modified-release preparations and formulations, for example, polymeric microsphere formulations, and oil- or gel-based formulations.

Sterile solutions may be prepared by combining the active compounds in the required amount in the appropriate solvent with other excipients as described above as required, followed by sterilisation, such as filtration. Generally, dispersions are prepared by incorporating the various sterilised active compounds into a sterile vehicle which contains the basic dispersion medium and the required excipients as described above. Sterile dry powders may be prepared by vacuum- or freeze-drying a sterile solution comprising the active compounds and other required excipients as described above.

With suitable stabilisation, for example N-to-C cyclisation, the peptides of the invention may be administered through oral routes of administration. Accordingly, other formulations for administration are contemplated by the present invention, including tablets, troches, capsules, elixirs, suspensions, syrups or wafers for oral delivery. Suitable components for such formulations are well known in the art.

Pharmaceutically acceptable vehicles and/or diluents include any and all solvents, dispersion media, coatings, antimicrobial agents, isotonic and absorption delaying agents. A skilled person would be familiar with suitable agents. Additional active ingredients may also be incorporated into the pharmaceutical compositions.

It is advantageous to formulate the compositions in dosage unit form for ease of administration and uniformity of dosage. The determination of the novel dosage unit forms of the present invention is dictated by and directly dependent on the unique characteristics of the active material, the particular therapeutic effect to be achieved and the limitations inherent in the art of compounding active materials for the treatment of disease in living subjects having a diseased condition in which bodily health is impaired as herein disclosed in detail.

As previously described, the active peptide is compounded for convenient and effective administration in effective amounts with a suitable pharmaceutically acceptable carrier in dosage unit form. In some embodiments, a unit dosage form may comprise the active peptide of the invention in amount in the range of from about 0.25 µg to about 2000 mg. The active peptide of the invention may be present in an amount of from about 0.25 µg to about 2000 mg/mL of carrier. In embodiments where the pharmaceutical composition comprises one or more additional active ingredients, the dosages are determined by reference to the usual dose and manner of administration of the said ingredients.

EXAMPLES

Certain embodiments of the invention will now be described with reference to the following examples, which are intended for the purpose of illustration only and are not intended to limit the scope of the generality hereinbefore described.

All materials and reagents used in the following examples are commercially available unless otherwise stated.

Example 1 Characterisation of Novel Spider Venom Peptides

Venoms from spiders were collected by mild electrical stimulation, then dried and kept frozen until use. To identify novel toxins that target primary afferent nociceptors, calcium imaging was used to screen a library of spider venoms for the ability to activate cultured somatosensory neurons.

Trigeminal ganglia (TG) were dissected from newborn (day 0 (P0) to day 3 (P3) post-natal) Sprague-Dawley rats and cultured for >12 hours before calcium imaging. Embryonic dorsal root ganglion (DRG) neuron cultures were maintained as described in Lewallen, et al. (2011) *Journal of Neuroscience*, 31(8): 3032-3043 and calcium imaging experiments were performed 1-10 days after primary cultures were established. For calcium imaging experiments, primary cells were plated onto cover slips coated with poly-L-lysine (Sigma) and laminin (Invitrogen, 10 µg/mL). Cells were loaded for calcium imaging with Fura-2-AM (Molecular Probes) for >1 hour. Buffer solution (150 mM NaCl, 2.8 mM KCl, 1 mM $MgSO_4$, 10 mM HEPES, pH adjusted to 7.4 with NaOH) was perfused with or without toxins/drugs using a SmartSquirt Micro-Perfusion system (AutoMate).

Trigeminal ganglia were dissected from newborn (P0-P3) C57BL/6 mice and dissociated with collagenase P (Sigma) and 0.25% Trypsin (15 minutes each). Cells were then triturated with a plastic pipette and cultured for >12 hours before electrophysiological recording. Whole-cell patch clamp recordings were performed manually on dissociated neurons using an Axopatch 200B amplifier (Axon instruments). Signals were digitized using a Digidata 1440A (Axon Instruments) and recorded using pClamp software. External solutions were 150 mM NaCl, 2.8 mM KCl, 1 mM $MgCl_2$, 1 mM $CaCl_2$), pH adjusted to 7.4 using NaOH. Internal solutions contained 130 mM K-gluconate, 15 mM KCl, 4 mM NaCl, 0.5 mM $CaCl_2$, 1 mM EGTA, 10 mM HEPES, pH adjusted to 7.2 using NaOH. Inward sodium channel currents were elicited by stepping the membrane voltage from −90 mV to −30 mV.

Venom from the tarantula *Heteroscodra maculata* robustly excited a subset of TG or DRG neurons.

To identify the active compounds, venom from *H. maculata* (1 mg dried) was fractionated on a $C_{18}$ reversed-phase (RP) high-performance liquid chromatography (HPLC) column (Jupiter 250×4.6 mm, 5 mm; Phenomenex, Torrance, Calif.) on a Shimadzu (Shimadzu, Rydalmere, NSW, Australia) Prominence HPLC system. The following linear gradients of solvent B (90% acetonitrile, 0.1% formic acid in water) in solvent A (0.1% formic acid in water) were used at a flow rate of 1 mL/min: 5% B for 5 min, then 5-20% B for 5 min followed by 20-40% B over 40 min. Absorbance was determined at 214 nm and 280 nm and collected fractions were lyophilized before storage at −20° C.

Venom fractionation yielded two active peaks, which were identified by matrix-assisted laser desorption/ionization mass spectrometry (MALDI MS) and Edman sequencing and were designated δ-theraphotoxin-Hm1a (Hm1a) and δ-theraphotoxin-Hm1b (Hm1b).

Peptide masses were determined by MALDI time-of-flight (TOF) MS using a 4700 Proteomics Bioanalyzer model (Applied Biosystems, Carlsbad, Calif.). Peptides were dissolved in water and mixed 1:1 (v/v) with alpha-cyano-4-hydroxycinnamic acid matrix (7 mg/ml in 50% acetonitrile, 5% formic acid) and mass spectra were acquired in positive reflector mode. All reported masses are for the monoisotopic M+H$^+$ ions.

N-terminal sequencing was performed by the Australian Proteome Analysis Facility (Sydney, NSW, Australia). In brief, Hm1a (600 pmol) and Hm1b (250 pmol) were reconstituted and reduced using DTT (25 mM) and left to incubate at 56° C. for 0.5 h. The samples were then alkylated using iodoacetamide (55 mM) at room temperature for 0.5 h and purified by RP-HPLC using a Zorbax 300SB-C18 column (3×150 mm). The target peaks of interest were identified, collected, then reduced to minimal volume under vacuum. The entire sample was loaded onto a precycled, Biobrene-treated disc and was subjected to 37 (Hm1a) or 42 (Hm1b) cycles of Edman N-terminal sequencing. Automated Edman degradation was carried out using an Applied Biosystems 494 Procise Protein Sequencing System.

Edman sequencing for Hm1a revealed the sequence ECRYLFGGCSSTSDCCKHLSCRSDWKYCAWDGTF [SEQ ID NO: 11], which has a calculated monoisotopic mass (for the M+H$^+$ ion) of 3908.58 Da. This is 89.97 Da lower than the monoisotopic mass of native Hm1a of 3995.55 Da. Hence, it was concluded that the C-terminal residue in Hm1a is serine, with a free carboxyl terminus, thus yielding the complete sequence of Hm1a as ECRYLFGGCSSTSDCCKHLSCRSDWKYCAWDGTFS-OH [SEQ ID NO: 4]. The complete sequence has a calculated monoisotopic mass (for the M+H⁺ ion) of 3995.61 Da, which is only 0.06 Da different to the mass measured for native Hm1a.

Edman sequencing for Hm1b revealed the sequence ECRYLFGGCKTTADCCKHLGCRTDLYYCAWDGT [SEQ ID NO: 12], which has a calculated monoisotopic mass (for the M+H⁺ ion) of 3745.6 Da. This is 147 Da lower than the monoisotopic mass of Hm1a of 3892.60 Da. Hence, it was concluded that the C-terminal residue in Hm1b is an amidated phenylalanine, thus yielding the complete sequence of Hm1b as ECRYLFGGCKTTADCCK-HLGCRTDLYYCAWDGTF-NH$_2$ [SEQ ID NO: 10]. The complete sequence has a calculated monoisotopic mass (for the M+H⁺ ion) of 3892.64 Da, which is only 0.04 Da different to the mass measured for native Hm1b.

Hm1a was synthesised using regioselective disulfide-bond formation. The peptide was assembled on a 0.1 mmol scale using a Symphony (Protein Technologies Inc.) automated peptide synthesiser and an H-Ser (tBu)-2-ClTrt (loading 0.69 mmol/g) resin. Fmoc deprotections were achieved using 30% piperidine/N,N-dimethylformamide (DMF) (1×1.5 min, then 1×4 min). Couplings were performed in DMF using 5 equivalents of Fmoc-amino acid/2-(1H-benzotriazol-1-yl)-1,1,3,3-tetramethyluronium hexafluorophosphate (HBTU)/N,N-diisopropylethylamine (DIEA) (1:1:1) relative to resin loading for 2×20 min. Non-cysteine amino acid side-chains were protected as Asp(OtBu), Arg(Pbf), Glu(OtBu), His (Trt), Lys(Boc), Ser (tBu), Thr (tBu), Trp (Boc), Tyr (tBu). The cysteine side chains were protected as Cys2,Cys16(Meb), Cys9, Cys21(Dpm), and Cys15, Cys28 (Trt). Cleavage from the resin was achieved by treatment with 10% acetic acid (AcOH)/10% triflurorethanol (TFE)/dichloromethane (DCM) at room temperature for 1 h. The product was precipitated and washed with n-hexane then lyophilised from 1,4-dioxane/acetonitrile (MeCN)/H$_2$O.

The first disulfide bond (Cys15-Cys28) was formed by dissolving the crude product in 1,1,1,3,3,3-hexafluoropropan-2-ol (HFIP) (5 mL) and adding dropwise to a stirred solution of I$_2$ (4 equiv) in 10% HFIP/DCM (20 mL) over 5 min. Stirring was continued for a further 5 min then the solution was poured into a solution of ascorbic acid/NaOAc in H$_2$O. The aqueous phase was extracted with DCM, and the combined organic layers washed with water (2×). Following removal of solvent under reduced pressure, the product was lyophilised from 1,4-dioxane/MeCN/H$_2$O. ESI-MS (m/z): calc. (avg) 2159.4 [M+3H]$^{3+}$, found 2159.7.

The second disulfide bond (Cys9-Cys21) was formed by first removing all of the remaining side chain protecting groups [except Cys (Meb)] by treating the product from the first step with 95% TFA/2.5% triisopropylsilane (TIPS)/2.5% H$_2$O at room temperature for 2 h to yield Cys2, Cys16(Meb), Cys9, Cys21(SH), Cys15-Cys28(SS) Hm1a (280 mg). ESI-MS (m/z): calc. (avg) 1404.3 [M+3H]$^{3+}$, found 1404.1. The crude product was then dissolved in 30% DMSO/0.1M HCl (0.5 mg/mL) and stirred at room temperature for 24 h. Cys2, 16(Meb), Cys9-Cys21(SS), Cys15-Cys28(SS) Hm1a was then isolated by preparative HPLC (30 mg). ESI-MS (m/z): calc. (avg) 1403.6 [M+3H]$^{3+}$, found 1403.3.

Formation of the third disulfide bond (Cys 2-Cys16) was then achieved by first removing the Cys (Meb) groups by treatment with HF/p-cresol (9:1) at 0° C. for 1 h. The product was precipitated and washed with cold Et$_2$O and lyophilised from 50% MeCN/0.1% TFA/H$_2$O yielding Cys2, 16(SH), Cys9-Cys21(SS), Cys15-Cys28(SS) Hm1a (24 mg). ESI-MS (m/z): calc. (avg) 1334.1 [M+3H]$^{3+}$, found 1333.7. Oxidation of the liberated thiols was performed using DMSO as described for the second disulfide bond to yield fully oxidised Hm1a (3 mg) that was indistinguishable by analytical HPLC from an authentic sample. ESI-MS (m/z): calc. (avg) 1333.5 [M+3H]$^{3+}$, found 1333.1.

Solvents for reversed-phase HPLC consisted of 0.05% TFA/H$_2$O (A) and 90% MeCN/0.043% TFA/H$_2$O (B). Analytical HPLC was performed on a Shimadzu LC20AT system using a Thermo Hypersil GOLD 2.1×100 mm C18 column heated at 40° C. with flow rate of 0.3 mL/min. A gradient of 10 to 55% B over 30 min was used, with detection at 214 nm. Preparative HPLC was performed on a Vydac 218TP1022 column running at a flow rate of 16 mL/min using a gradient of 10 to 50% B over 40 min. Mass spectrometry was performed on an API2000 (ABI Sciex) mass spectrometer in positive ion mode.

Application of synthetic Hm1a to TG neurons triggered calcium responses (FIG. 1a), validating these peptides as active venom components. All subsequent experiments involving Hm1a were performed with synthetic Hm1a peptide.

Tetrodotoxin (TTX) blocked Hm1a-evoked calcium responses (FIG. 1a), suggesting involvement of voltage-gated sodium (Na$_v$) channels. Indeed, whole-cell patch-clamp recordings from TG neurons showed that Hm1a robustly inhibited sodium channel inactivation (FIG. 1b).

Somatosensory neurons express several Na$_v$ subtypes, including Na$_v$1.1, 1.6, 1.7, 1.8, and 1.9. However, only Na$_v$1.1, 1.6 and 1.7 are sensitive to TTX. ICA-121431, a small molecule inhibitor with selectivity for Na$_v$1.1 and 1.3 subtypes, was found to greatly diminish calcium responses induced by Hm1a, suggesting that among the major sensory neuron subtypes, Na$_v$1.1 is the main target of Hm1a (FIGS. 1c and 1d). In contrast, ICA-121431 did not attenuate responses to SGTx1, an Hm1a-related peptide that shows little selectivity among Na$_v$ subtypes and, not surprisingly, excited a larger cohort of TG neurons.

Inhibition of Na$_v$ inactivation should render cells hyperexcitable without directly altering resting membrane potential. Indeed, analysis of Hm1a-responsive TG neurons in whole-cell current clamp configuration showed this to be the case (FIG. 1e). Hm1a did not alter resting membrane potential (before Hm1a, Vm=−55±6 mV; after Hm1a, Vm=−56±6 mV), but it robustly enhanced spike frequency following a 20 pA current injection. Hm1a also prolonged the action potential waveform, consistent with introduction of non-inactivating sodium current (FIG. 1e).

Example 2 Biophysical Properties of Hm1a and Hm1b

To characterize the functional activity of Hm1a and Hm1b, HEK293T cells stably transfected with either hSCN1A, hSCN2A, hSCN3A, hSCN5A, hSCN9A or hSCN10A as well as CHO cells stably transfected with hSCN4A or hSCN8A were used for whole-cell patch-clamp analysis with a high throughput automated planar patch-clamp technology.

HEK293T cells stably transfected with either hSCN1A, hSCN2A, hSCN3A, hSCN5A, hSCN9A or hSCN10A were maintained in Dulbecco's Modified Eagle's Medium Nutrient Mixture F-12 (Invitrogen, Carlsbad, Calif., USA) supplemented with 10% (v/v) foetal bovine serum (FBS) (Invitrogen), 0.9% Penicillin/Streptomycin (P/S) solution and 100 µg/mL hygromycin or 100 µg/mL neomycin. CHO cells stably transfected with hSCN4A or hSCN8A were maintained in Ham's F12 Nutrient Mixture (Invitrogen, Carlsbad, Calif., USA) supplemented with 10% (v/v) FBS, 0.9% P/S solution and 100 µg/mL hygromycin. All cells were grown in T75 flasks (BD Biosciences, San Jose, Calif., USA) to ~70% confluency.

Patch-clamp recordings were conducted in the whole-cell configuration using a Patchliner® (Nanion Technologies, Munich, Germany). Before recordings, cells were detached from culture flasks with Accutase Cell Detachment Solution (Innovative Cell Technologies Inc., San Diego, Calif., USA) and resuspended at a density of $1 \times 10^6$ to $5 \times 10^7$ per milliliter in 50% serum free media and 50% external recording solution v/v. The external recording solution comprised: 140 mM NaCl, 4 mM KCl, 1 mM $MgCl_2$, 2 mM $CaCl_2$), 5 mM D-glucose, 10 mM HEPES (pH adjusted to 7.4 with NaOH). The osmolarity of this solution was 298 mOsm. The internal recording solution comprised: 50 mM CsCl, 10 mM NaCl, 60 mM CsF, 2 mM $MgCl_2$, 20 mM EGTA, 10 mM HEPES (pH adjusted to 7.2 with CsOH) and the osmolarity of this solution was 285 mOsm. Solutions were filtered using a 0.2 jm membrane filter (Minisart; Sartorius Stedim Biotech, Goettingen, Germany). Cells were kept in suspension by gentle automatic pipetting. Test peptide was dissolved in $H_2O$ with 0.1% fatty-acid free BSA (fafBSA) (Sigma-Aldrich, Castle Hill, NSW). Medium single-hole planar NPC-16 chips with an average resistance of ~2.5 MΩ were used. Pipette and whole cell capacitance were fully compensated and the series resistance compensation was set to 50%. Recordings were acquired at 50 kHz with the low pass filter set to 3 kHz in PATCHMASTER (HEKA Instruments Inc., NY, USA) and performed at 27° C. When data needed further filtering for the analysis of sustained current, recordings were additionally filtered at 500 Hz offline using a Gaussian filter algorithm. Offline analysis was performed using Microsoft Excel, MatLab and GraphPad Prism 6 (Molecular Devices). Data are shown as means±S.E.M. Leak subtraction was performed in software before the currents were normalised. Statistical analysis was performed using Student's t-test and differences were considered significant when $p<0.05$.

The voltage dependence of activation was studied by measuring the normalised peak currents during 100 ms depolarisations from −120 mV to +30 mV in 5 mV increments. The resulting current-voltage curve was fit to the equation $I=[1+exp(-0.03937 \cdot z \cdot (V-V_{1/2})]/g \cdot (V-V_r)$, where I is current amplitude; z is apparent gating charge; V is test potential; $V_{1/2}$ is half maximal voltage; g is a factor related to the maximum number of open channels; and $V_r$ is reversal potential. Conductance was determined using $G=I/(V-V_r)$, where G is conductance. The conductance values were then fit with the Boltzmann equation $G=1/(1+exp[(V-V_{1/2})/a])$, where a is the slope of the half-maximum, V is the potential of the given pulse and $V_{1/2}$ is the potential for the half-maximal activation. To study steady-state fast inactivation, cells were held at conditioning pre-pulse potentials ranging from −120 mV to +30 mV in 5 mV increments from a holding potential of −120 mV and a test pulse at 0 mV for 20 ms. The peak current amplitudes during the subsequent test pulses were normalised to the peak current amplitude during the first test pulse and plotted against the potential of the conditioning pulse and fitted with the Boltzmann equation $I=1/(1+exp[(V-V_{1/2})/a])$. Recovery from fast inactivation was studied by pre-pulsing the cells to 0 mV from a holding potential of −120 mV for 30 ms to fully inactivate channels. The voltage was then returned to the holding potential of −120 mV for variable intervals (every 3 ms from 0 to 39 ms). Finally, the voltage was stepped to 0 mV for 30 ms to test channel availability. The peak current amplitude during the test potentials was plotted as fractional recovery against the recovery period by normalising to the maximum current during the conditioning potentials. The recovery currents were plotted against delta time. Inactivation time constants were determined using MATLAB R2015a (Mathworks, MA, USA). Scripts were written that identified the peak current of each trace. A single exponential curve was used to fit each trace $I=A \cdot exp[-(t-K)/\tau]+C$, where I is the current, A is the relative proportion of the current inactivating with the time constant τ, K is the time shift, and C is the steady-state persistent current. The time constants were plotted against voltage and the points on this graph were fitted with a decaying exponential equation $Y=span*exp(-K*x)+plateau$, where span is the starting point of the curve, K is the decay factor and plateau is the value the curve decays to.

To examine the effects of synthetic Hm1a (Example 1) or native Hm1b, cells were held at −120 mV and 20 or 100 ms test depolarisations to 0 mV were applied every 2 s for 60 s in the presence of vehicle control (0.1% fafBSA). The cells were then exposed to 1, 5 or 50 nM Hm1a or Hm1b sequentially for 2 min. Currents for individual cells were averaged over 30 s periods directly before application of Hm1a or Hm1b, and following two minutes exposure to 1, 5 and 50 nM Hm1a or Hm1b.

The representative raw current traces in FIG. 2 illustrate the effects of Hm1a on the different human voltage-gated sodium channel isoforms ($hNa_v1.1$-$hNa_v1.8$) examined in this study. External application of Hm1a causes a minimal increase in the peak current amplitude of $hNa_v1.1$, but it potently inhibits $hNa_v1.1$ inactivation in a dose-dependent manner, leading to a large increase in sustained current. To a lesser extent Hm1a slows the rate of inactivation of $hNa_v1.3$, but this does not result in a sustained current. Hm1a has no effect on the other $hNa_v$ subtypes at the concentrations tested (up to 50 nM).

Next, the effect of synthetic Hm1a (Example 1) and native Hm1b on the biophysical properties of $hNa_v1.1$ was examined.

Typical current family traces illustrate the potent inhibitory effect of 5 nM Hm1a on $hNa_v1.1$ channel inactivation (FIG. 3*a*). FIG. 3*b* shows the voltage-dependence of activation and inactivation between vehicle control (BSA, ●), 5 nM Hm1a (○) and 50 nM Hm1a (Δ). Hm1a causes a hyperpolarizing shift in the voltage-dependence of steady-state activation of $hNa_v1.1$, suggesting that it might be easier to activate the channel in the presence of peptide. The peptide has no significant effect on the $V_{1/2}$ or the slope of the inactivation curve for $hNa_v1.1$, suggesting that it does not alter the voltage-dependence of fast inactivation. The data points were fit with a Boltzmann equation and the $V_{1/2}$ and slope values were obtained (Table 4). The hyperpolarising shift in the $V_{1/2}$ was significant for the activation curves at 5 nM and 50 nM Hm1a compared to vehicle, although the slope of the activation curve was not significantly different from vehicle. The V. and slope of the inactivation curve were not altered by Hm1a when compared to vehicle. These data indicate that Hm1a has little or no effect on the steady-state voltage dependence of inactivation of the $hNa_v1.1$ current, despite its ability to delay entry into fast inactivation of this channel.

TABLE 4

Biophysical parameters for activation and inactivation for hNa$_v$1.1

| | Voltage-dependence of activation | | | Voltage-dependence of inactivation | | |
|---|---|---|---|---|---|---|
| | $V_{1/2}$ (mV) | Slope | n | $V_{1/2}$ (mV) | Slope | n |
| Vehicle | −2.6 ± 0.2 | 10.0 ± 0.7 | 6 | −28.8 ± 1.4 | 9.7 ± 0.3 | 6 |
| Hm1a 1 nM | −8.1 ± 0.4 | 10.6 ± 0.9 | 6 | −30.7 ± 1.0 | 9.0 ± 0.2 | 6 |
| Hm1a 5 nM | −13.3 ± 0.9* | 9.4 ± 0.4 | 6 | −33.4 ± 1.1 | 9.7 ± 0.4 | 6 |
| Hm1a 50 nM | −12.3 ± 1.0* | 11.8 ± 1.3 | 6 | −29.6 ± 1.2 | 11.9 ± 0.8 | 6 |

Values are presented as mean ± standard error. Statistical significance is marked as
*p < 0.05.
Comparisons were made between the vehicle control and Hm1a at the three concentrations tested.

Figure 3:
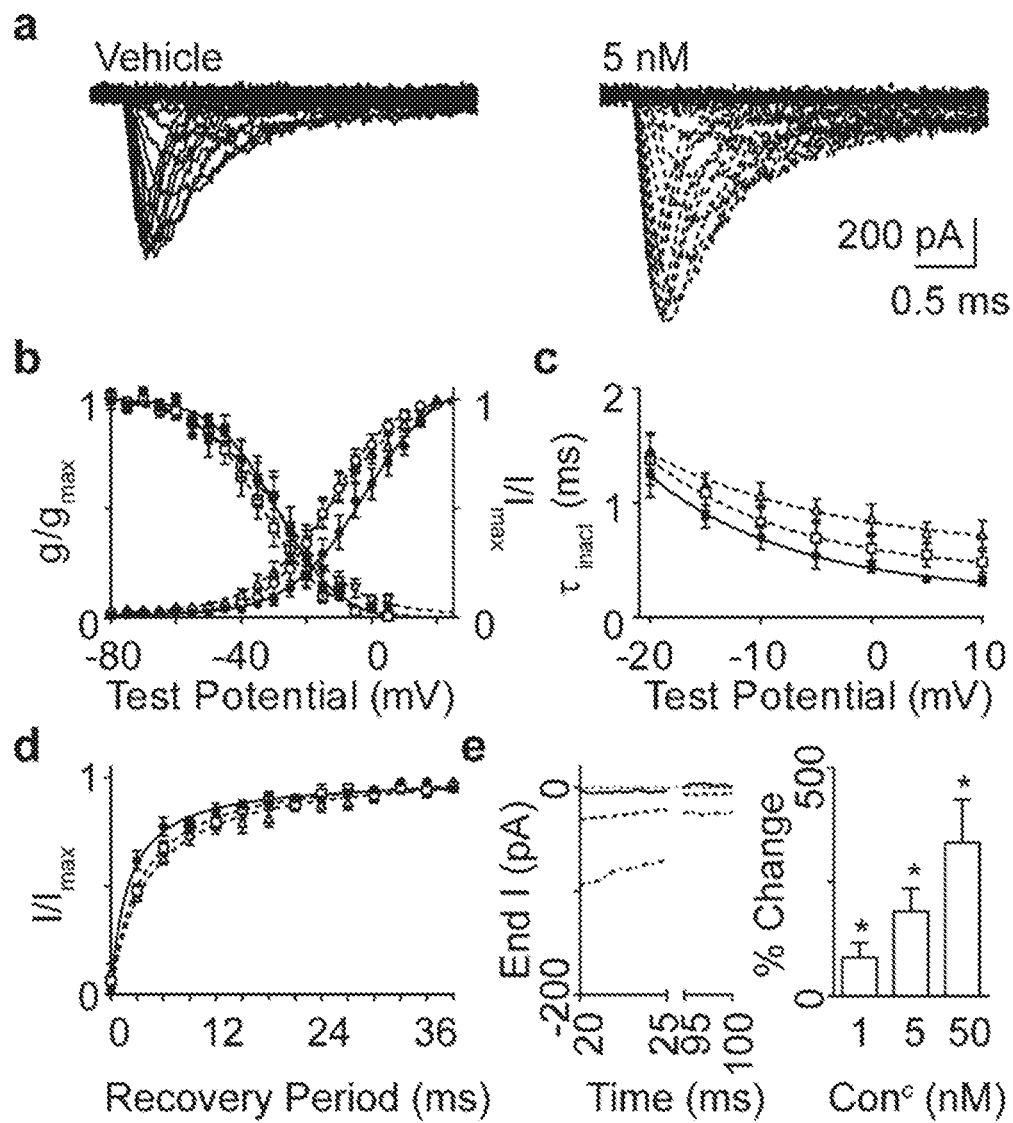
FIG. 3 Effect of Hm1a on the biophysical properties of the hNa$_v$1.1 channel. a. Representative raw current-family traces for hNa$_v$1.1 in the presence of vehicle control (left; solid line) and 5 nM Hm1a (right; dashed lined). b. Voltage-dependence of normalized peak conductance and steady-state inactivation. Normalized conductance (activation; left axis) shown for hNa$_v$1.1 in the presence of vehicle (●), 5 nM Hm1a (○) and 50 nM Hm1a (Δ), as a function of voltage (n=6). Steady-state fast-inactivation shown for hNa$_v$1.1 (right axis) in the presence of vehicle (●), 5 nM Hm1a (○) and 50 nM Hm1a (∇). c. Time constant of fast-inactivation shown for hNa$_v$1.1 in the presence of vehicle (0), 5 nM Hm1a (□) and 50 nM Hm1a (Δ), as a function of voltage. Current for each cell was fitted to a single exponential at a range of test potentials and a time constant was determined. A one phase exponential decay was fit to pooled averages and plotted (n=6). d. Recovery of channel availability from fast-inactivation shown for hNa$_v$1.1 in the presence of vehicle (●), 5 nM Hm1a (□) and 50 nM Hm1a (Δ), as a function of time. A hyperbola was fitted to pooled averages and plotted (n=6). e. Sustained currents at two different time points shown for hNa$_v$1.1 in the presence of vehicle (solid line), 5 nM Hm1a (dashed line) and 50 nM Hm1a (dashed dotted line). Mean percent change in end current for hNa$_v$1.1 in the presence of 1, and 50 nM Hm1a (n=6). Statistical significance is marked as *p<0.05. Comparisons were made between the vehicle control and Hm1a (1, 5 and 50 nM).

FIG. 3c shows the time constant (τ) of fast inactivation at a range of voltages for vehicle control (●), and 5 nM (○) and 50 nM (Δ) Hm1a. At concentrations of 5 nM and 50 nM, Hm1a significantly increases the time constants at potentials more positive than −5 mV (Table 5).

TABLE 5

Biophysical parameters for the time constant of fast inactivation for hNa$_v$1.1

| | Time constant of fast inactivation | | | |
|---|---|---|---|---|
| | Span | K | Plateau | n |
| Vehicle | 1.0 ± 0.2 | 0.08 ± 0.01 | 0.25 ± 0.07 | 6 |
| Hm1a 1 nM | 1.2 ± 0.3 | 0.11 ± 0.02 | 0.30 ± 0.02 | 6 |
| Hm1a 5 nM | 0.9 ± 0.4 | 0.07 ± 0.01 | 0.47 ± 0.03* | 6 |
| Hm1a 50 nM | 0.8 ± 0.1 | 0.09 ± 0.02 | 0.75 ± 0.1* | 6 |

Values are presented as mean ± standard error.
Statistical significance is marked as
*p < 0.05.
Comparisons were made between the vehicle control and Hm1a.

FIG. 3d shows normalised hNa$_v$1.1 current as a function of time following an inactivating voltage step in the presence of vehicle (●), 5 nM Hm1a (○) and 50 nM Hm1a (Δ). Hm1a significantly slows channel recovery compared to vehicle. The curves were fit with a hyperbola as a means to characterise the data, for which the recovery constants were significantly increased in the presence of 5 nM and 50 nM, but not 1 nM Hm1a when compared to vehicle (Table 6), suggestive of a slower transition from the inactivated to closed channel state.

TABLE 6

Biophysical parameters for recovery of channel availability from fast inactivation for Na$_v$1.1

| | Recovery from inactivation | | |
|---|---|---|---|
| | $I_{max}$ | Time constant (rc) | n |
| Vehicle | 1.01 ± 0.01 | 1.98 ± 0.2 | 6 |
| Hm1a 1 nM | 0.99 ± 0.01 | 1.74 ± 0.2 | 6 |
| Hm1a 5 nM | 1.03 ± 0.02 | 3.35 ± 0.3* | 6 |
| Hm1a 50 nM | 1.04 ± 0.02 | 4.07 ± 0.4* | 6 |

Values are presented as mean ± standard error.
Statistical significance is marked as
*p < 0.05.
Comparisons were made between the vehicle control and Hm1a.

FIG. 3e shows the hNa$_v$1.1 sustained currents at two different time points following application of Hm1a. There is no sustained current in the presence of the vehicle. However, after 24 ms the emergence of a sustained current is apparent in the presence of 5 nM and especially 50 nM Hm1a. Furthermore this sustained current is still substantial at the end of the 100 ms voltage step.

Figure 4:
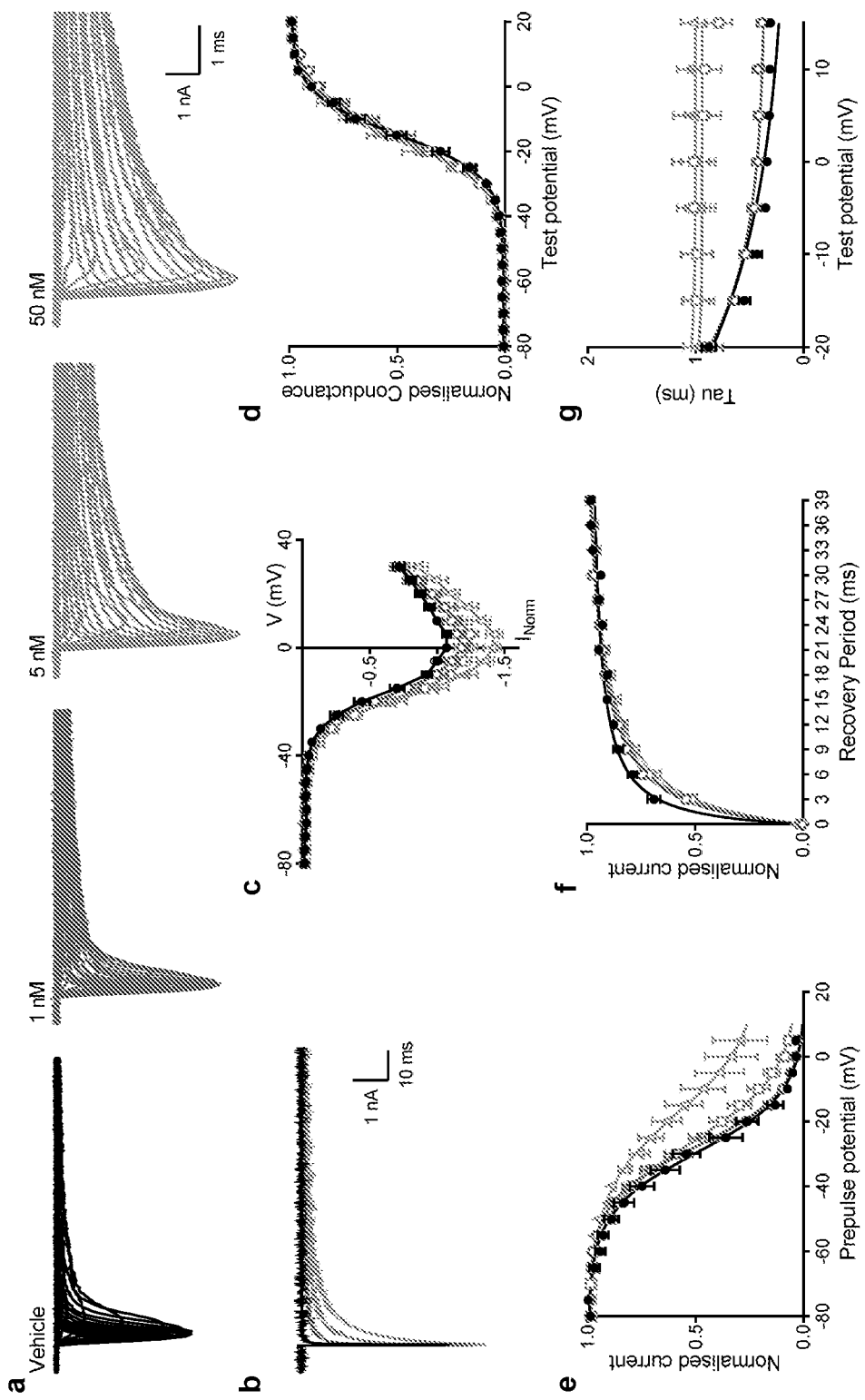
FIG. 4 Effect of Hm1b on the biophysical properties of the hNa$_v$1.1 channel. a. Representative raw current-family traces for hNa$_v$1.1 in the presence of vehicle (■), 1 nM Hm1b (■), 5 nM Hm1b (■) and 50 nM Hm1b (■). Scale bars apply to all traces. b. Representative raw current traces for hNa$_v$1.1 in the presence of vehicle control (■), 1 nM Hm1b (■), 5 nM Hm1b (■) and 50 nM Hm1b (■). Traces are averaged over 30 s periods. c. Normalised current-voltage relationship curves shown for hNa$_v$1.1 in the presence of vehicle (●), 1 nM Hm1b (○), 5 nM Hm1b (□) and 50 nM Hm1b (Δ)(n=8). d. Normalised peak conductance shown for hNa$_v$1.1 in the presence of vehicle (●), 1 nM Hm1b (○), 5 nM Hm1b (□) and 50 nM Hm1b (Δ), as a function of voltage (n=8). e. Steady-state fast-inactivation shown for hNa$_v$1.1 in the presence of vehicle (●), 1 nM Hm1b (○), 5 nM Hm1b (□) and 50 nM Hm1b (Δ)(n=8). f. Recovery of channel availability from fast-inactivation shown for hNa$_v$1.1 in the presence of vehicle (●), 1 nM Hm1b (○), 5 nM Hm1b (□) and 50 nM Hm1b (Δ), as a function of time. A hyperbola was fitted to pooled averages and plotted (n=8). g. Time constant of fast-inactivation shown for hNa$_v$1.1 in the presence of vehicle (●), 1 nM Hm1b (○), 5 nM Hm1b (□) and 50 nM Hm1b (Δ), as a function of voltage. Current for each cell was fitted to a single exponential at a range of test potentials and a time constant was determined. A one phase exponential decay was fit to pooled averages and plotted (n=8).

Similarly to Hm1a, native Hm1b (1, 5 or 50 nM) potently inhibits hNa$_v$1.1 channel inactivation (FIGS. 4a, 4b and 4c), causes a slight hyperpolarizing shift in the voltage-dependence of steady-state activation of hNa$_v$1.1 and does not appear to alter the voltage-dependence of fast inactivation of hNa$_v$1.1 (FIGS. 4d and 4e). Normalised hNa$_v$1.1 current as a function of time following an inactivating voltage step is plotted in FIG. 4f, which shows vehicle and Hm1b (1, 5 and 50 nM). Hm1b slows channel recovery compared to vehicle. FIG. 4g shows the time constant (i) of fast inactivation at a range of voltages for vehicle control and Hm1b at different concentrations. At concentrations of 5 nM and 50 nM, Hm1b increases the time constants at potentials more positive than −15 mV.

Example 3 Hm1a Activity in GABAergic Neurons from Dravet Syndrome Mice

Mice (post-natal day 14-16) were anaesthetized using isoflurane and sacrificed by decapitation. Brain slices (300-μm thick) were cut using a vibratome in the sagittal plane. Slices were kept at room temperature until recording. The slices were transferred to a recording chamber constantly perfused at 34° C. with artificial cerebrospinal fluid (CSF) solution consisting of: 125 mM NaCl, 2.5 mM KCl, 25 mM NaHCO$_3$, 1.25 mM NaH$_2$PO$_4$, 1 mM MgCl$_2$, 2 mM CaCl$_2$) and 10 mM glucose, aerated with 95% O$_2$ and 5% CO$_2$ (final pH of 7.4). Whole-cell patch-clamp recordings were made using a MultiClamp 700A amplifier and pClamp acquisition software (Molecular Devices) from neurons visually identified using infrared differential interference contrast imaging (BX51, Olympus). Electrodes were pulled using a Sutter P-2000 puller (Sutter Instruments) from borosilicate micropipettes (World Precision Instruments) with an initial resistance of ~2-3 megaohms and filled with intracellular solution consisting of 125 mM KGlu, 4 mM KCl, 2 mM MgCl$_2$, 10 mM HEPES, 10 mM EGTA, 4 mM ATP-Mg, 0.3 mM GTP-Na, and 8 mM Biocytin Hydrochloride adjusted to a final pH of 7.3 with KOH. D-Mannitol was used to adjust osmolarity to 300 mOsm. Bridge balance was applied to all recordings. Voltage recordings were filtered at 30 kHz and sampled at 100 kHz. A holding current was injected into neurons if required, setting their holding potential to approximately −75 mV. A current injection/action potential (AP) frequency relationship was established by injecting an 800 ms square pulse of progressively depolarising currents. An automated AP detection algorithm in Axograph was used to detect AP with visual confirmation. The integrated number of APs between injection current bins of the i-o relationships was calculated (Axograph X) in order to allow comparison between control and Hm1a. AP threshold voltage was defined as the voltage at which velocity reached 10 mV/ms. For the AP waveform analysis, amplitude was measured from threshold to peak, rise-time was determined as the time between 10% to 90% of the AP amplitude and AP width was measured at 50% of the peak amplitude. AP measured at 'collapse' were selected for each individual cell at the first current injection at which AP collapse was robust. APs at the same current injection were analyzed in the presence of Hm1a. Membrane input resistance was measured in current clamp mode by measuring the last 200 ms of the voltage trace generated by a current injection of −10 pA.

Figure 5:
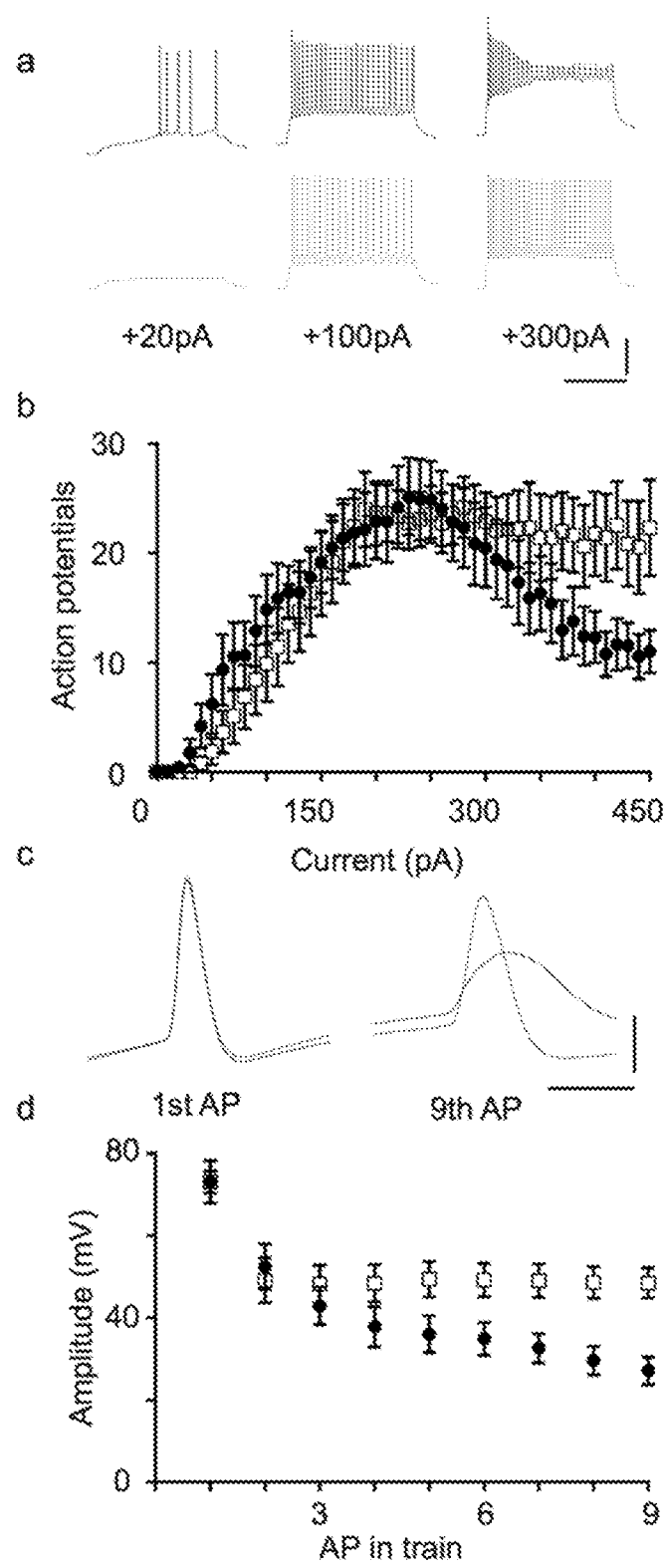
FIG. 5 Effect of Hm1a on 'action potential (AP) firing collapse' in SCN1A (R1407X) CA1 GABAergic neurons. a. Top panel: raw traces recorded from single SCN1A (R1407X) CA1 GABAergic neuron at progressively more depolarizing current injections. Bottom panel: raw traces from the same neuron following the addition of 10 nM Hm1a. b. Summary of stimulus current-action potential firing (i-o) data shows the recovery of 'AP collapse' in the presence of 10 nM Hm1a (□) compared with the control (●) (p=0.02, n=10; paired t-test, t=2.678, df=9). c. Raw traces (control in black and Hm1a in grey) of the 1$^{st}$ and 9$^{th}$ individual AP from a train of APs at the point of collapse. d. Summary of peak AP amplitude of sequential APs in a train for control (●) and 10 nM Hm1a (□). Scale bars in a: horizontal=400 ms, vertical=35 mV.

Whole-cell recordings were made from CA1 GABAergic neurons obtained from SCN1A (R1407X) Dravet syndrome mice, identified by their position within the molecular layers, and an input current versus AP firing rate relationship established. AP firing collapse in GABAergic interneurons was a robust cellular phenotype (FIG. 5a, b). Hm1a (10 nM) rescued AP firing at current injections that caused 'AP collapse' with average APs significantly greater than control for current injections between 300 and 450 pA (FIG. 5b, $p=0.02$, n=10; paired t-test, t=2.678, df=9). A small but significant right-shift in rheobase was also observed on application of Hm1a (p=0.001, n=10; paired t-test, t=4.714, df=9). Hm1a had no impact on resting potential (Table 7) or input resistance (550±73 versus 460±60 MΩ, p=0.11, n=10) of the SCN1A (R1407X) GABAergic neurons.

Further, no changes were seen in any of the morphology measurements of APs analysed at rheobase (Table 7).

TABLE 7

Action potential morphology analysis at rheobase in GABAergic neurons isolated from Dravet syndrome mice

| n = 10 | Amp (mV) | Rise (ms) | Width (ms) | Threshold (mV) | RMP (mV) |
|---|---|---|---|---|---|
| Control | 70 ± 2 | 0.76 ± 0.06 | 1.8 ± 0.2 | −44 ± 2 | 73 ± 2 |
| Hm1a 10 nM | 71 ±4 | 0.71 ± 0.04 | 1.9 ± 0.2 | −36 ± 4 | 72 ± 2 |

Values are presented as mean ± standard error.

To further test the impact of Hm1a on firing, we performed a detailed analysis of the individual AP morphology of the first nine detected APs around the point of collapse of each neuron (FIGS. 5c and 5d). While there was no significant change in the morphology of the first two APs, Hm1a significantly increased the maximal amplitude of subsequent APs in a train (FIG. 5d) essentially rescuing the collapsing phenotype seen in the mutant Dravet syndrome mouse (9th AP; 27.1±0.1 mV versus 48.4±3.1 mV for control, p=0.005, n=10).

A faster rise-time (9th AP; 1.7±0.2 ms versus 1.3±0.1, p=0.05, n=10) and shorter half-width (9th AP; 4.3±0.4 ms versus 3.0±0.4, p=0.07, n=10; FIG. 5c) was also evident for later APs in the presence of the peptide. This suggests that Hm1a specifically reverses the AP collapsing deficit proposed as the underlying basis of neuronal excitability in the Dravet mouse model.

Figure 6:
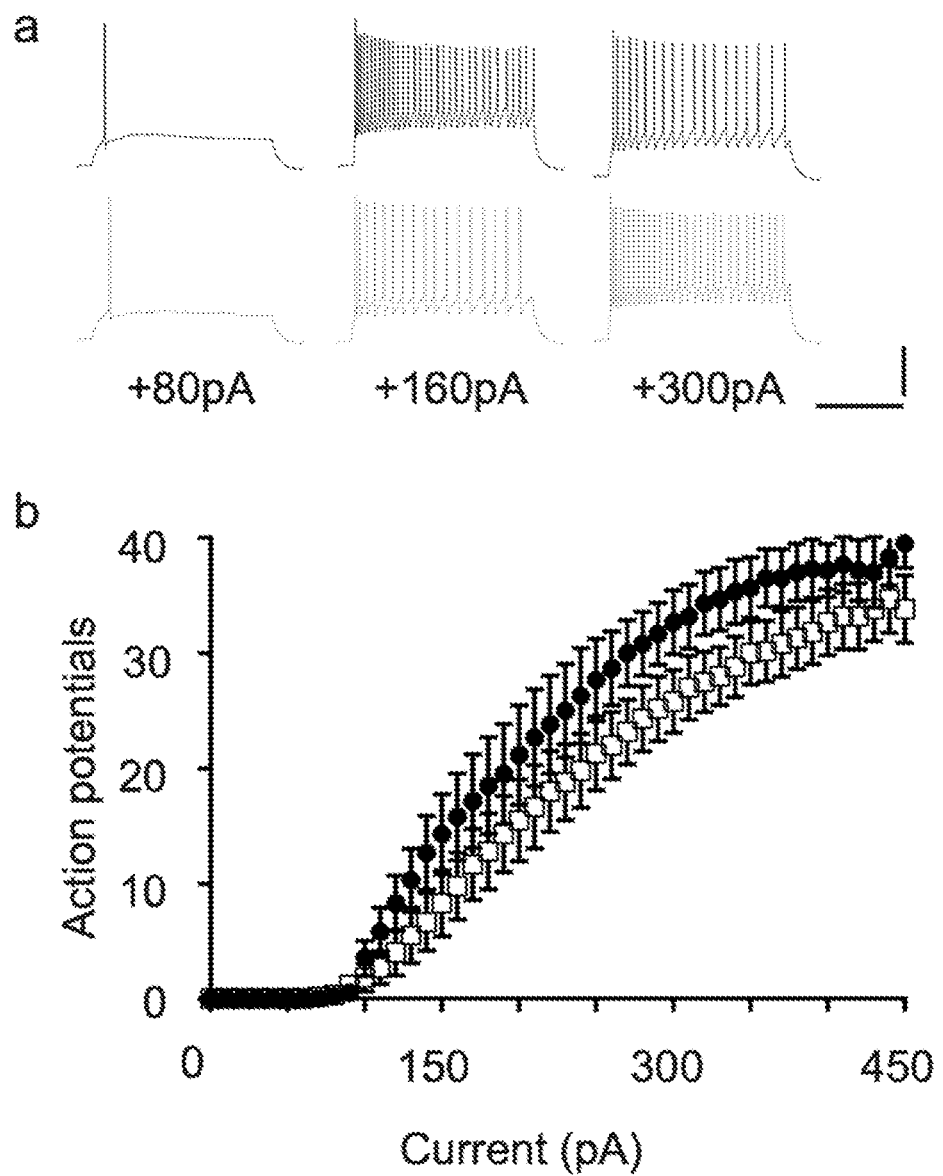
FIG. 6 Impact of Hm1a on AP firing in wild-type CA1 inhibitory interneurons. a. Top panel: raw traces recorded from single wild-type CA1 inhibitory interneurons at progressively more depolarizing current injections. Bottom panel: raw traces from the same neuron following the addition of 10 nM Hm1a. b. Summary of i-o data indicates a small right shift in the relationship at higher current injections in the presence of 10 nM Hm1a (□) compared with control (●). Scale bars in a: horizontal=400 ms, vertical=40 mV.

The impact of the peptide on non-collapsing wild-type CA1 GABAergic inhibitory interneurons was also tested (FIG. 6). There was no shift in the rheobase on application of Hm1a but there was a small right shift in the current-AP relationship at intermediate current injections that normalized at higher currents (FIG. 6b). Hm1a had no impact on resting potential (Table 8) or input resistance (270±40 versus 330±40 MΩ, p=0.76, n=6) of the wild-type GABAergic inhibitory neurons. Further, no changes in any of the morphology measurements of APs analysed at rheobase were seen (Table 8).

TABLE 8

Action potential morphology analysis at rheobase in wildtype GABAergic neurons

| n = 6 | Amp (mV) | Rise (ms) | Width (ms) | Threshold (mV) | RMP (mV) |
|---|---|---|---|---|---|
| Control | 79 ± 9 | 0.49 ± 0.6 | 1.4 ± 0.1 | −44 ± 3 | 79 ± 2 |
| Hm1a 10 nM | 79 ± 8 | 0.43 ± 0.4 | 1.3 ± 0.1 | −38 ± 2 | 79 ± 2 |

Values are presented as mean ± standard error.
RMP = resting membrane potential.

Example 4 Hm1a Activity in Excitatory Neurons

Figure 7:
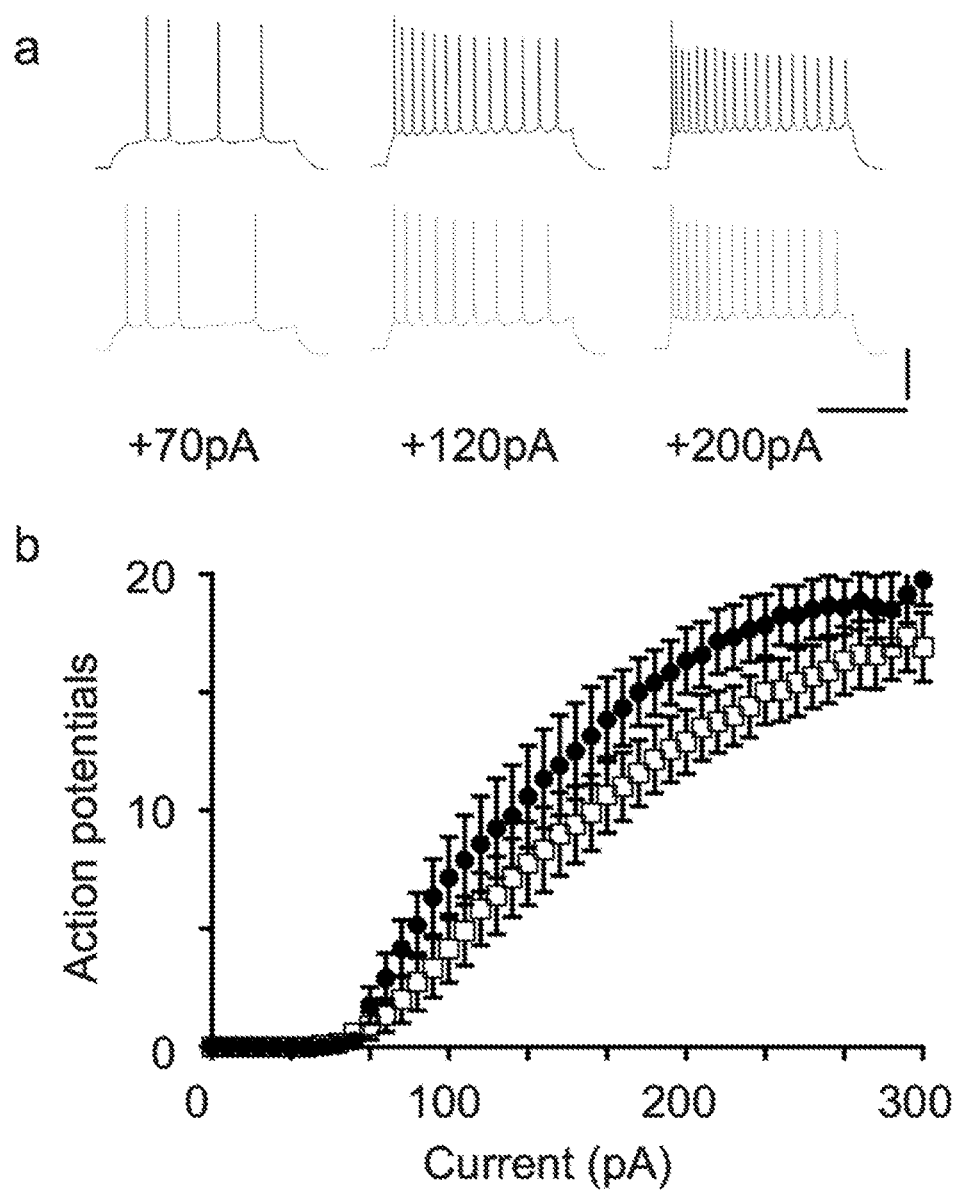
FIG. 7 Impact of Hm1a on AP firing in SCN1A (R1407X) CA1 pyramidal neurons. a. Top panel: raw traces recorded from single wild-type CA1 pyramidal neuron at progressively more depolarizing current injections. Bottom panel: raw traces from the same neuron following the addition of 10 nM Hm1a. b. Summary of i-o data indicates a small right shift in the relationship at intermediate current injections in the presence of 10 nM Hm1a (□) compared with control (●). Scale bars: horizontal=400 ms, vertical=35 mV.

To test the impact of synthetic Hm1a (Example 1) on excitatory neurons, whole-cell recordings were made from CA1 pyramidal neurons isolated from SCN1A (R1407X) Dravet syndrome mice. The input current versus AP firing rate relationship was not altered by the application of 10 nM Hm1a (FIG. 7). Hm1a had no impact on resting potential (Table 9) or input resistance (450±70 versus 420±60 MΩ, p=0.8, n=6) of the pyramidal neurons. Additionally, no changes were seen in the morphology of APs analysed at rheobase (Table 9).

TABLE 9

Action potential morphology at rheobase in pyramidal neurons from SCN1A (R1407X) Dravet syndrome mice

| n = 6 | Amp (mV) | Rise (ms) | Width (ms) | Threshold (mV) | RMP (mV) |
|---|---|---|---|---|---|
| Control | 99 ± 3 | 0.45 ± 0.03 | 2.1 ± 0.2 | −48.2 ± 2.9 | 75 ± 2 |
| Hm1a 10 nM | 97 ± 4 | 0.46 ± 0.05 | 2.1 ± 0.1 | −43.1 ± 3.1 | 73 ± 2 |

Values are presented as mean ± standard error.
RMP = resting membrane potential.

Example 5 Impact of Hm1a on Interical Spiking in Dravet Syndrome Mice

Heterozygous SCN1A (R1407X) Dravet syndrome mice and wild-type littermates underwent ECoG and intracerebroventricular (ICV) guide cannula implantation surgery at post-natal day 18. ECoG surgery was as previously described in Reid, et al. (2011) Epilepsia, 52 (1): 115-120. In addition, a guide cannula was implanted during the surgery positioned in the right ventricle using a Kopf® stereotaxic frame with the following coordinates from bregma: caudal −0.4 mm and lateral 1.0 mm; 2.0 mm from the skull. At least 24 hours recovery was allowed following surgery before commencing ECoG recording and simultaneous infusion of either peptide or vehicle alone delivered via ICV. A total volume of 5 μL of peptide (0.5 mM) was infused, suspended in vehicle containing 0.1% BSA and sterile saline; control animals received 5 μL of vehicle only. Synthetic Hm1a (Example 1) or vehicle only was infused (0.1 μL/minute) via an internal cannula connected to a Hamilton syringe and driver (Harvard PHD 2000). Placement of ICV cannula and injection site was validated using dye delivered via the right ventricle and post-hoc analysis of experimental animals.

ECoG and video recordings were made for unrestrained animals at least one hour prior to ICV peptide delivery and then an additional 2-3 hours after infusion using Powerlab 16/30 (AD Instruments Pty. Ltd., Sydney, NSW, Australia); signals were band-pass filtered at 0.1 to 200 Hz and sampled at 1 kHz. A criterion for measurement of interictal spikes was amplitude at least 2 times greater than standard deviation of background ECoG signal. Data was analysed using Sirenia Seizure Pro (1.6.6; Pinnacle Technology).

Figure 8:
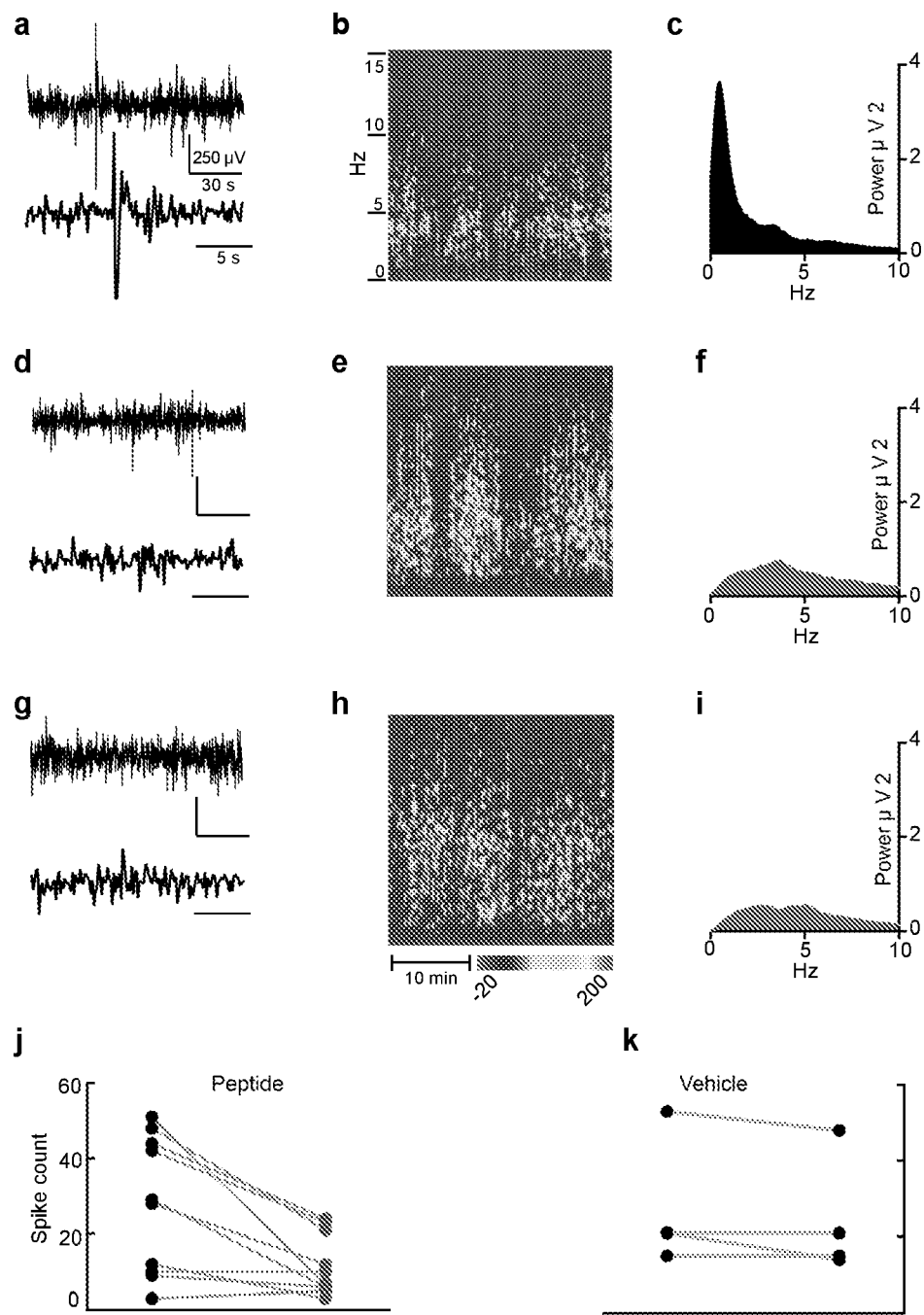
FIG. 8 Effect of Hm1a on epileptiform discharges in Dravet syndrome (DS) mice. a. Interictal electrocorticography (ECoG) recordings: Raw trace from DS mouse at postnatal day 20 (P20) before peptide delivery. Two-minute ECoG raw trace from extended 30-minute epoch analysis shows high amplitude interictal spike events used to measure Hm1a efficacy. b. Power spectrum analysis for 30-min epoch and frequency components calculated by conventional fast Fourier transformation (FFT) and spectral plots shown in the right column for power ($\mu V^2$) versus frequency (Hz). c. Peak activity shown at 0.5-2 Hz prior to Hm1a delivery. d-f. ECoG spike analysis from same animal after Hm1a infusion; d. Raw trace shows reduced spike amplitude; expanded 30 minute epoch of e ECoG power spectrum and f corresponding spectral plot show markedly reduced ECoG activity in 0.5-2 Hz frequency range. g-i. Wild-type animal aged P20 ECoG data for comparison to SCN1A (R1407X) ECoG analysis; g. Wild-type ECoG raw trace without epileptiform discharges. h. The power spectrum and i spectral plot for wild-type mice were similar to data acquired for SCN1A (R1407X) mice after Hm1a treatment. j. Mean spike count for SCN1A (R1407X) mice was significantly reduced after Hm1a infusion (n=10; p=0.006). Each pair of connected points represents a single mouse. k. No significant change was detected for vehicle infusion alone (n=4; p=0.2). Each pair of connected points represents a single mouse.

Seizure frequency and severity were analysed using continuous video monitoring in SCN1A (R1407X) Dravet syndrome mice (n>10), which revealed that the majority of mice died between P18 and P21 following a generalised tonic-clonic seizure. Interictal epileptiform discharges (spikes) were used as a measure of Hm1a efficacy, combining microelectrode recordings before, during and after peptide delivery as a biomarker of brain hyper-excitability in Dravet syndrome mice aged P19-P21 (FIG. 8a). Power spectrum analysis showed peak activity at 0.5-2 Hz visualized using heat maps (FIG. 8b) and spectral plots (FIG. 8c). Activity was reduced after Hm1a delivery to the same animal as shown by raw ECoG trace (FIG. 8d); 30 min epoch heat map (FIG. 8e) and spectral plot (FIG. 8f). An example analysis for comparison to a wild-type mouse ECoG recording is shown (FIG. 8g-i). The number of high amplitude interictal spikes during 30 min epoch before Hm1a delivery (28±6; n=10) was significantly reduced after Hm1a administration (12±2; p=0.0059; FIG. 8j). No significant change in spike count during 30 min epoch was found before delivery of vehicle only (27±9; n=4) compared to after vehicle delivery (24±8; p=0.19; FIG. 8k).

Example 6 Hm1b Activity at hNa$_v$1.2, hNa$_v$1.3 and hNa$_v$1.6

To further characterise the functional activity of Hm1b, HEK293T cells stably transfected with hSCN2A and hSCN3A as well as CHO cells stably transfected with hSCN8A were used for whole-cell patch-clamp analysis with a high throughput automated planar patch-clamp technology.

HEK293T cells stably transfected with hSCN2A and hSCN3A and CHO cells stably transfected with hSCN8A were maintained as described in Example 2. The patch-clamp assay and pulse protocols were also conducted as previously described in Example 2.

To examine the effects of native Hm1b, cells were held at −120 mV and 20 ms test depolarisations to 0 mV were applied every 2 s for 60 s in the presence of vehicle control (0.1% fafBSA). The cells were then exposed to 1 nM, 5 nM or 50 nM Hm1b sequentially for 2 minutes.

Figure 9:
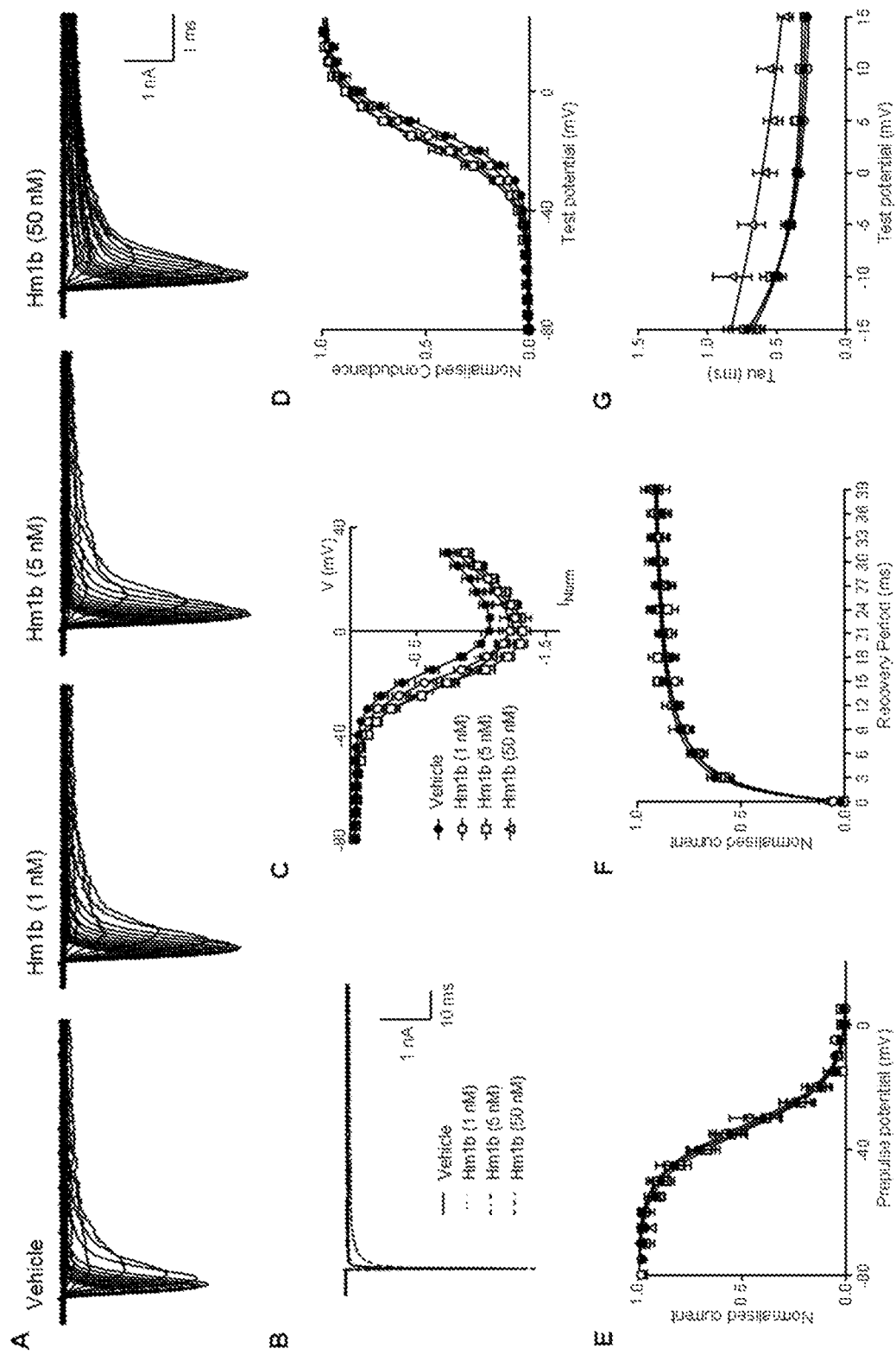
FIG. 9 Effect of Hm1b on the biophysical properties of the hNa$_v$1.2 channel. A. Representative raw current-family traces for hNa$_v$1.2 in the presence of vehicle control, 1 nM Hm1b, 5 nM Hm1b and 50 nM Hm1b. Scale bars apply to all traces. B. Mean representative current traces in the presence of vehicle control (solid line), 1 nM Hm1b (dotted line), 5 nM Hm1b (dot-dash line) and 50 nM Hm1b (dashed line). C. Normalised current-voltage relationship curves shown for hNa$_v$1.2 in the presence of vehicle (●), 1 nM Hm1b (○), 5 nM Hm1b (□) and 50 nM Hm1b (Δ) (n=7 cells). D. Normalised conductance shown for hNa$_v$1.2 in the presence of vehicle (●), 1 nM Hm1b (○), 5 nM Hm1b (□) and 50 nM Hm1b (Δ), as a function of voltage (n=7 cells). E. Steady-state fast-inactivation shown for hNa$_v$1.2 in the presence of vehicle (●), 1 nM Hm1b (○), 5 nM Hm1b (□) and 50 nM Hm1b (Δ), as a function of voltage (n=7 cells). F. Recovery of channel availability from fast-inactivation shown for hNa$_v$1.2 in the presence of vehicle (●), 1 nM Hm1b (○), 5 nM Hm1b (□) and 50 nM Hm1b (Δ), as a function of time (n=7 cells). A hyperbola was fitted to pooled averages and plotted. G. Time constant of fast-inactivation shown for hNa$_v$1.2 in the presence of vehicle (●), 1 nM Hm1b (○), 5 nM Hm1b (□) and 50 nM Hm1b (Δ), as a function of voltage (n=7 cells). Current for each cell was fitted to a single exponential at a range of test potentials and a time constant was determined. A one phase exponential decay was fit to pooled averages and plotted.
Figure 10:
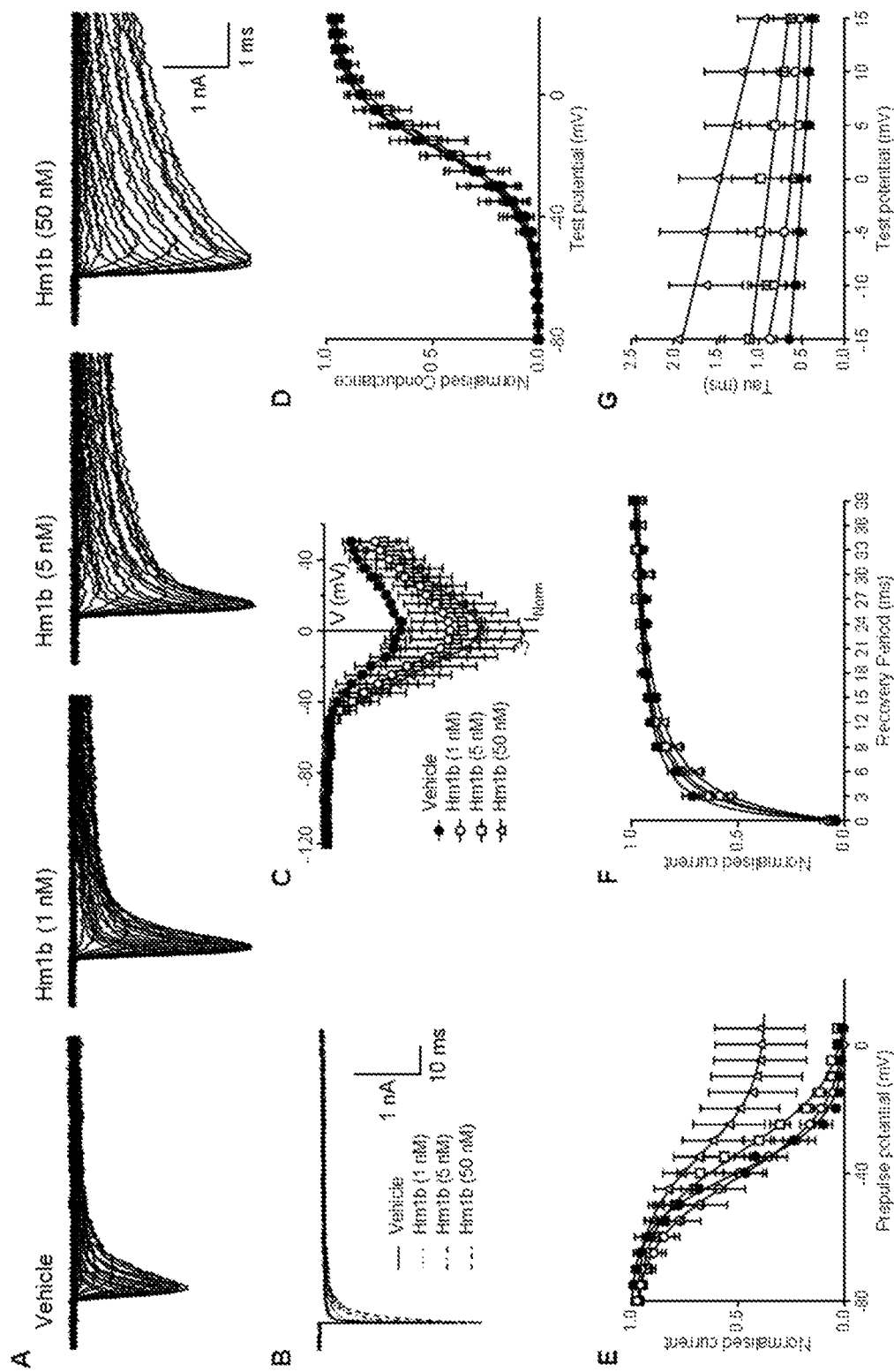
FIG. 10 Effect of Hm1b on the biophysical properties of the hNa$_v$1.3 channel. A. Representative raw current-family traces for hNa$_v$1.3 in the presence of vehicle control, 1 nM Hm1b, 5 nM Hm1b and 50 nM Hm1b. Scale bars apply to all traces. B. Mean representative current traces in the presence of vehicle control (solid line), 1 nM Hm1b (dotted line), 5 nM Hm1b (dot-dash line) and 50 nM Hm1b (dashed line). C. Normalised current-voltage relationship curves shown for $hNa_v1.3$ in the presence of vehicle (●), 1 nM Hm1b (○), 5 nM Hm1b (□) and 50 nM Hm1b (Δ) (n=5 cells). D. Normalised conductance shown for $hNa_v1.3$ in the presence of vehicle (●), 1 nM (○), 5 nM (□) and 50 nM (Δ) Hm1b, as a function of voltage (n=5 cells). E. Steady-state fast-inactivation shown for $hNa_v1.3$ in the presence of vehicle (●), 1 nM Hm1b (○), 5 nM Hm1b (□) and 50 nM Hm1b (Δ), as a function of voltage (n=5 cells). F. Recovery of channel availability from fast-inactivation shown for $hNa_v1.3$ in the presence of vehicle (●), 1 nM Hm1b (○), 5 nM Hm1b (□) and 50 nM Hm1b (A), as a function of time (n=5 cells). A hyperbola was fitted to pooled averages and plotted. G. Time constant of fast-inactivation shown for $hNa_v1.3$ in the presence of vehicle (●), 1 nM Hm1b (○), 5 nM Hm1b (□) and 50 nM Hm1b (Δ), as a function of voltage (n=5 cells). Current for each cell was fitted to a single exponential at a range of test potentials and a time constant was determined. A one phase exponential decay was fit to pooled averages and plotted.
Figure 11:
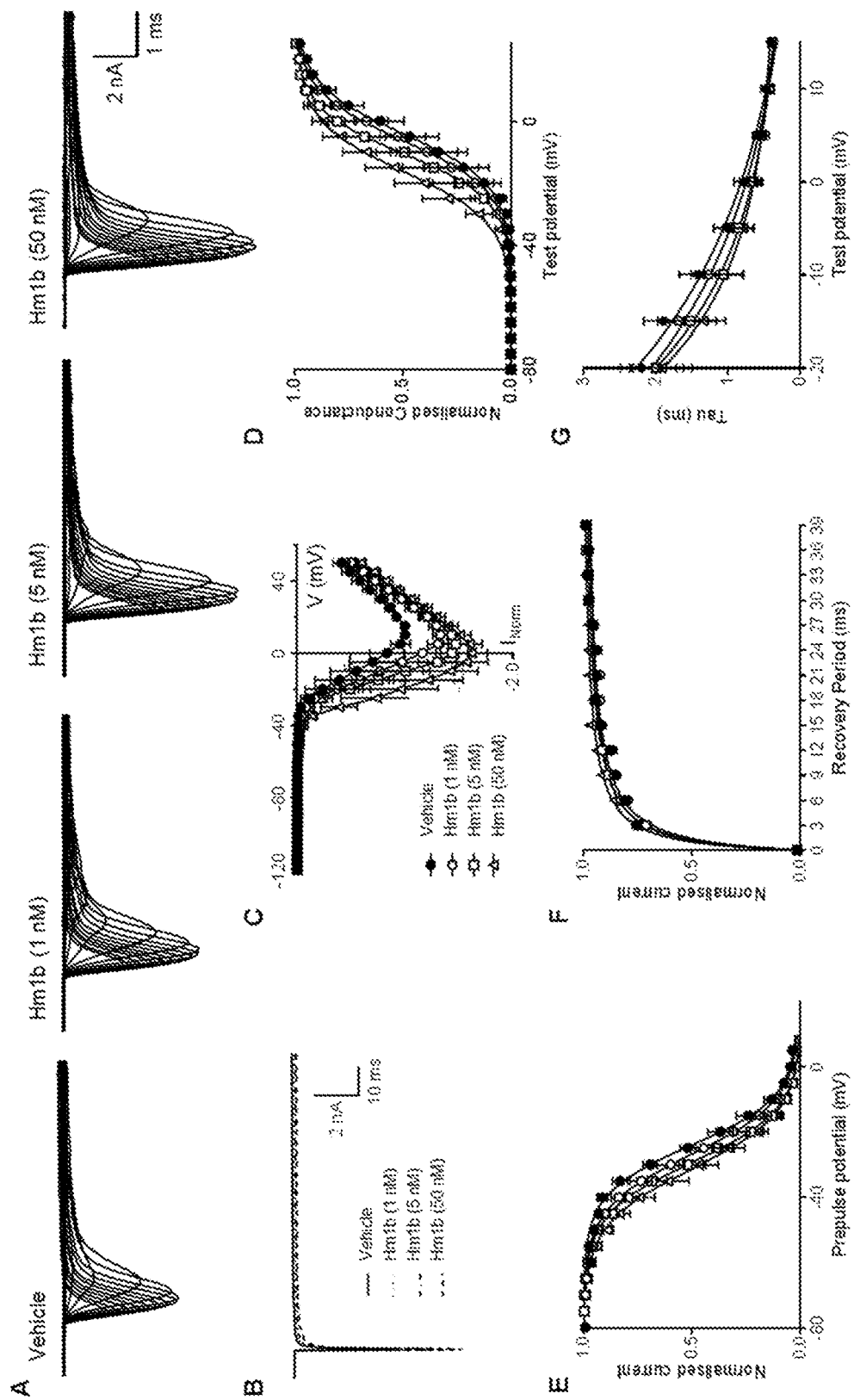
FIG. 11 Effect of Hm1b on the biophysical properties of the $hNa_y1.6$ channel. A. Representative raw current-family traces for $hNa_v1.6$ in the presence of vehicle control, 1 nM Hm1b, 5 nM Hm1b and 50 nM Hm1b. Scale bars apply to all traces. B. Mean representative current traces in the presence of vehicle control (solid line), 1 nM Hm1b (dotted line), 5 nM Hm1b (dot-dash line) and 50 nM Hm1b (dashed line). C. Normalised current-voltage relationship curves shown for $hNa_v1.6$ in the presence of vehicle (●), 1 nM Hm1b (○), 5 nM Hm1b (□) and 50 nM Hm1b (Δ) (n=6 cells). D. Normalised conductance shown for $hNa_v1.6$ in the presence of vehicle (●), 1 nM Hm1b (○), 5 nM Hm1b (□) and 50 nM Hm1b (Δ), as a function of voltage (n=6 cells). E. Steady-state fast-inactivation shown for $hNa_v1.6$ in the presence of vehicle (●), 1 nM Hm1b (○), 5 nM Hm1b (□) and 50 nM Hm1b (Δ), as a function of voltage (n=6 cells). F. Recovery of channel availability from fast-inactivation shown for $hNa_v1.6$ in the presence of vehicle (●), 1 nM Hm1b (○), 5 nM Hm1b (□) and 50 nM Hm1b (Δ), as a function of time (n=6 cells). A hyperbola was fitted to pooled averages and plotted. G. Time constant of fast-inactivation shown for $hNa_v1.6$ in the presence of vehicle (●), 1 nM Hm1b (○), 5 nM Hm1b (□) and 50 nM Hm1b (Δ), as a function of voltage (n=6 cells). Current for each cell was fitted to a single exponential at a range of test potentials and a time constant was determined. A one phase exponential decay was fit to pooled averages and plotted.

Hm1b did not have a significant effect on hNa$_v$1.2 channel inactivation (FIGS. 9a, 9b and 9c). 5 nM and 50 nM Hm1b appeared to have a slight inhibitory effect on hNa$_v$1.3 and, to a lesser extent, hNa$_v$1.6 channel inactivation (FIGS. 10a, 10b, 10c, 11a, 11b and 11c). Hm1b does not appear to alter the voltage-dependence of fast inactivation of hNa$_v$1.2, 1.3 and 1.6 (FIGS. 9d, 9e, 10d, 10e, 11d and 11e). Normalised hNa$_v$1.2, 1.3 and 1.6 current as a function of time following an inactivating voltage step is plotted in FIGS. 9f, 10f and 11f, respectively. Hm1b does not appear to slow hNa$_v$1.2 and hNa$_v$1.6 channel recovery compared to vehicle (FIGS. 9f and 11f), but appears to slow hNa$_v$1.3 channel recovery compared to vehicle at higher concentrations (FIG. 10f). FIGS. 9g, 10g and 11g examine the time constant (τ) of fast inactivation at a range of voltages for vehicle control and 1 nM, nM and 50 nM Hm1b. 50 nM Hm1b increases the time constants of fast inactivation of hNa$_v$1.2 at potentials more positive than −10 mV (FIG. 9g), and 5 nM and 50 nM Hm1b increased the time constants of fast inactivation of hNa$_v$1.3 at potentials more positive than −15 mV (FIG. 10g). Hm1b did not have an effect on the time constants of fast inactivation of hNa$_v$1.6 (FIG. 11g).

Example 7 Recombinant Hm1b Activity at hNa$_v$1.1-1.7

Hm1b was produced recombinantly in *Escherichia coli*. Due to the production method used, recombinant Hm1b contains an additional serine residue on the N-terminus and has a C-terminal acid, in comparison with a C-terminal amide in the native peptide. The sequence of recombinant Hm1b is as below:

[SEQ ID NO: 8]
SECRYLFGGCKTTADCCKHLGCRTDLYYCAWDGTF-OH.

A synthetic gene encoding recombinant Hm1b, with codons optimised for *E. coli*, was produced and subcloned into a pLIC-MBP expression vector by GeneArt (Invitrogen, Regensburg, Germany). This plasmid enables expression of Hm1b as a His$_6$-tagged maltose binding protein (MBP) fusion protein (i.e. His$_6$-MBP-Hm1b). The plasmid was transformed into *E. coli* strain BL21 (λDE3) for recombinant peptide expression.

Transformed BL21 cells were grown in Luria-Bertani medium containing 100 μg/ml ampicillin at 37° C. with shaking at 140 rpm. Peptide expression was induced with 250 μM IPTG, then the cell culture was incubated overnight at 16° C., before harvesting cells by centrifugation at 6000 rpm for 15 min at 4° C. The His$_6$-MBP-Hm1b fusion protein was extracted by cell disruption at 32 kPa (TS Series Cell Disruptor, Constant Systems Ltd, UK), and then captured by passing the extract (buffered in 20 mM Tris, 200 mM NaCl, pH 8.0) over Ni-NTA super flow resin (QIAGEN, Chadstone, Australia). Nonspecific protein binders were removed by washing the column with 15 mM imidazole then the fusion protein was eluted with 400 mM imidazole.

The eluted fusion protein was concentrated to 5 mL, and incubated at room temperature for 12 hours on a shaker with His$_6$-tagged TEV protease (1 mg/mL) in the presence of reduced and oxidized glutathione (0.6 mM GSH/0.4 mM GSSG, respectively) (Sigma-Aldrich). The cleaved His$_6$-MBP and His$_6$-TEV protease were precipitated by addition of 1% trifluoroacetic acid (TFA), then the sample was centrifuged at 4000 rpm. The supernatant was filtered using a 0.22 μm syringe filter (Millipore, MA, USA) and subjected to further purification using reverse-phase (RP) HPLC. RP-HPLC was performed on a Phenomenex Jupiter C4 column (250×10 mm, particle size 10 μm) at a flow rate of 1.0 ml/min first, followed by further purification using a Phenomenex Aeris C$_{18}$ column (250×4.6 mm, particle size 3.6 μm) at a flow rate of 0.75 mL/min with a gradient of 20-40% solvent B (0.043% TFA in 90% acetonitrile) in solvent A (0.05% TFA in water) over 40 min.

The activity of recombinant Hm1b was assessed at hNa$_v$1.1-1.7. Sodium currents were measured from hNa$_v$ channels stably expressed in HEK293 cells using an automated whole-cell patch-clamp electrophysiology system (QPatch 16X; Sophion, Ballerup, Denmark). The extracellular solution comprised 2 mM CaCl$_2$), 1 mM MgCl$_2$, 10 mM HEPES, 4 mM KCl, 145 mM NaCl, 10 mM D-glucose at pH 7.3, and 305 mOsm. The intracellular solution comprised 140 mM CsF, 1 mM/5 mM EGTA/CsOH, 10 mM HEPES, 10 mM NaCl at pH 7.3, osmolality 320 mOsm. The elicited currents were sampled at 25 kHz and filtered at 5 kHz. Cells were maintained at a holding potential of −80 mV and sodium currents were elicited by 210 ms voltage steps at 0 mV after a 50 ms conditioning step from −120 mV. For dose-response experiments, cells were incubated for 5 min with increasing concentrations of Hm1b. Peptide stock solutions were made up to 10 μM and serial dilutions were prepared in extracellular solution containing 0.1% BSA. Graphs and fittings were performed using Prism 7.0 (GraphPad Software, San Diego, Calif.). Numerical data are presented as mean SEM based on at least three experiments (n≥3).

Figure 12:
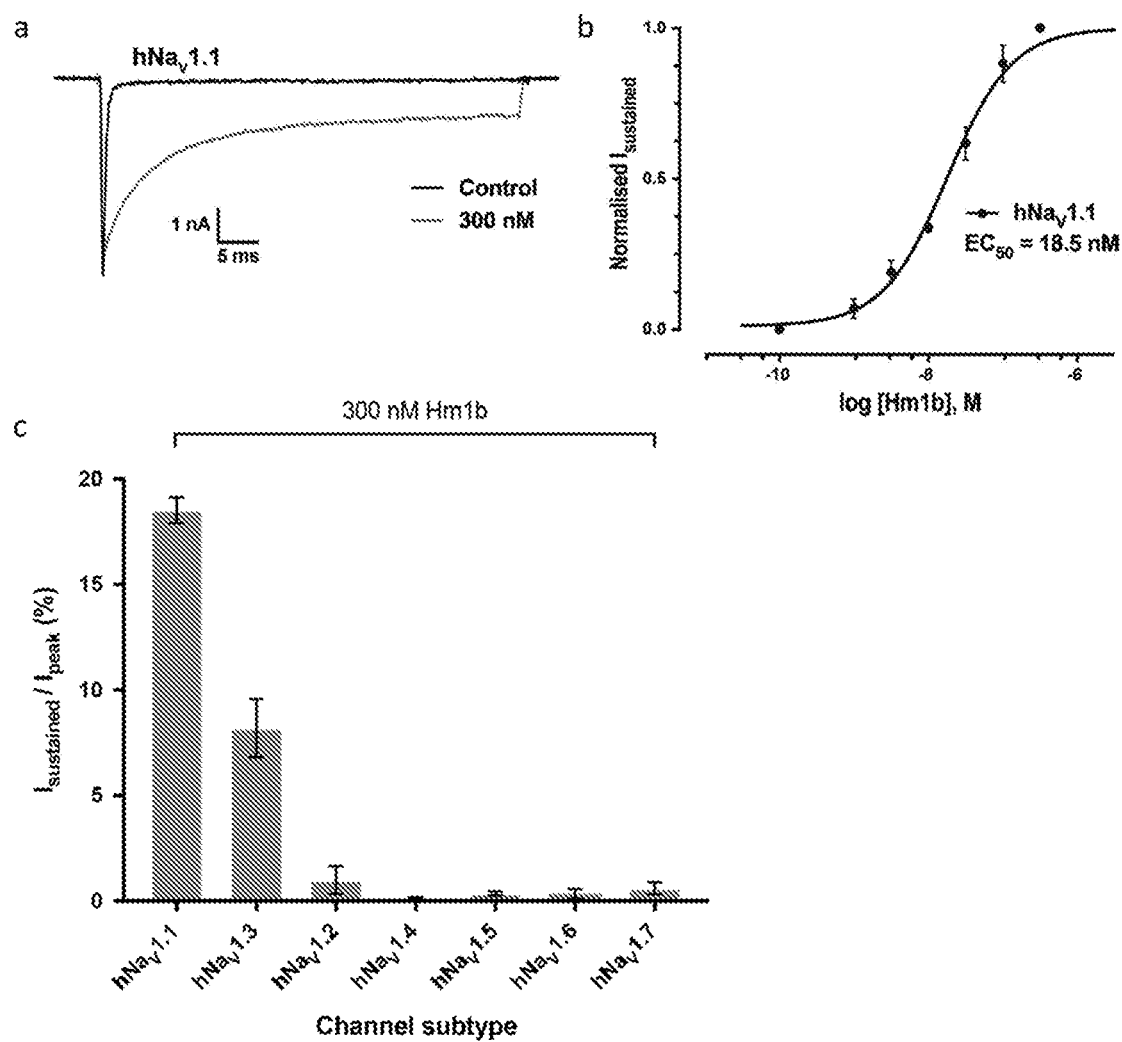
FIG. 12 Effect of recombinant Hm1b on human voltage-gated sodium channel subtypes, $hNa_v1.1$-1.7, stably expressed in HEK293 cells. a. Representative raw current traces for $hNa_v1.1$ stably expressed in HEK293 cells in the presence of vehicle or 300 nM recombinant Hm1b. b. Dose-response curve for recombinant Hm1b at $hNa_v1.1$ stably expressed in HEK293 cells (n=3). c. Histogram comparing the ability of recombinant Hm1b (300 nM) to evoke sustained currents at $hNa_v1.1$-1.7.

Compared to control conditions, a saturating concentration of recombinant Hm1b (300 nM) delayed fast inactivation and induced a sustained current at the end of the depolarising pulse in HEK293 cells stably expressing hNa$_v$1.1 (FIG. 12a). Recombinant Hm1b potently evoked sustained currents at hNa$_v$1.1 with an EC$_{50}$ of 18.5 nM (FIG. 12b), and it showed a very high level of selectivity for hNa$_v$1.1 over hNa$_v$1.2, hNa$_v$1.4, hNa$_v$1.5, hNa$_v$1.6 and hNa$_v$1.7, and to a lesser extent hNa$_v$1.3 (FIG. 12c).

Example 8 Recombinant Hm1b[K11S] Activity at hNa$_v$1.1

The effect of recombinant Hm1b with lysine at position 11 mutated to serine (recombinant Hm1b[K11S]) on hNa$_v$1.1 activity was assessed. The sequence of recombinant Hm1b [K11S] is as below:

[SEQ ID NO: 9]
SECRYLFGGCSTTADCCKHLGCRTDLYYCAWDGTF-OH.

The point mutation (Lys to Ser at position 11) was introduced into the pLIC-MBP-Hm1b expression plasmid (produced according to the methods of Example 7) by polymerase chain reaction (PCR) using mutagenic primers and standard protocols with Platinum Pfx DNA Polymerase (Invitrogen). Mutagenic primers were designed using the online tool PrimerX and synthesised by Integrated DNA Technologies, Inc. (Emu Heights, NSW). DNA from the mutant construct was isolated and sequenced to verify the desired mutation (AGRF, Brisbane, Australia). Plasmid DNA was isolated using ISOLATE II plasmid Mini Kit (Bioline, London, UK) for transformation into *E. coli* BL21 cells for recombinant peptide production. Recombinant Hm1b[K11S] was expressed using the procedure of Example 7. The activity of recombinant Hm1b[K11S] was assessed at hNa$_v$1.1 in accordance with the procedure of Example 7.

Figure 13:
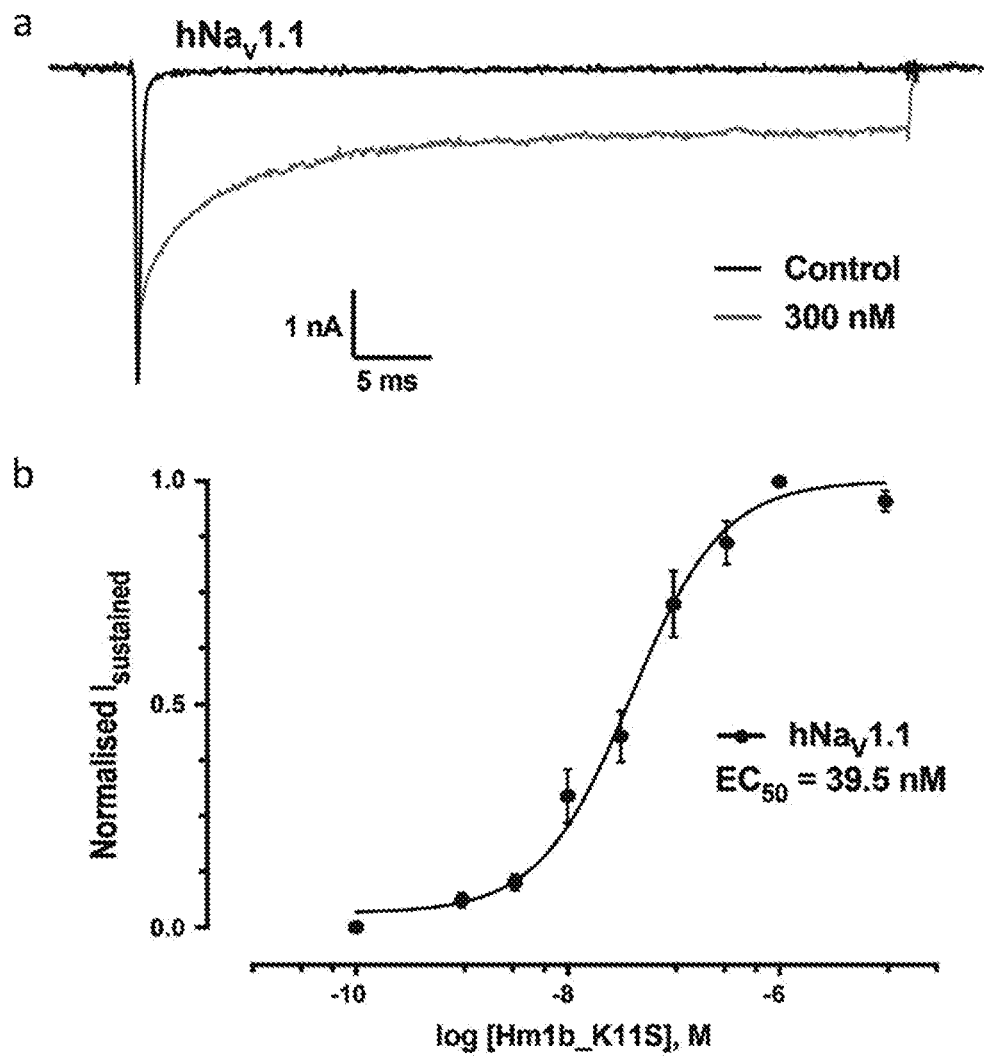
FIG. 13 Effect of recombinant Hm1b[K11S] on the $hNa_v1.1$ channel, stably expressed in HEK293 cells. a. Representative raw current traces for $hNa_v1.1$ stably expressed in HEK293 cells in the presence of vehicle or 300 nM recombinant Hm1b[K11S]. b. Dose-response curve for recombinant Hm1b[K11S] at $hNa_v1.1$ stably expressed in HEK293 cells (n=3).

Recombinant Hm1b[K11S] delayed fast inactivation of hNa$_v$1.1 and induced a sustained current at the end of the depolarising pulse in HEK293 cells stably expressing hNa$_v$1.1 (FIG. 13a). The ability of recombinant Hm1b [K11S] to evoked sustained currents at hNa$_v$1.1 (EC$_{50}$=39.5 nM; FIG. 13b) was similar to that of native Hm1a (FIG. 12b).

Example 9 Stability of Hm1a and Hm1b in Human Cerebrospinal Fluid (CSF)

The stability of Hm1a and Hm1b in human cerebrospinal fluid (CSF) was compared to the human analgesic drug ω-conotoxin MVIIA, also known as ziconitide (ω-conotoxin), and human atrial natriuretic peptide 1-28 (hANP). 1.8 μg native Hm1a, 1.8 μg recombinant Hm1b (produced in accordance with Example 7), 1.2 μg ω-conotoxin MVIIA (commercially available) and 1.4 μg hANP (commercially available) were added to CSF at a final concentration of 1 μM and incubated at 37° C. for a period of up to 72 hrs. Triplicate samples were collected at each time point. Collected samples were precipitated by the addition of 5 μL of 5% TFA. 10 μL of sample from each time point was then analysed using LC/MS using a Kinetex C$_{18}$ column (150 mm×2.1 mm, particle size 2.6 μm, 100 Å pore size) at a flow of 0.2 mL/min and a gradient of 2-40% solvent B (90% acetonitrile, 0.1% formic acid) in solvent A (0.1% formic acid) over 14 min coupled with an AB SCIEX 5600 TripleTOF mass spectrometer (cycle time 0.2751 s). Integrated areas of peaks corresponding to intact peptide were measured at triple-, quadruple- and quintuple charge states, and were analysed using PeakView and MultiQuant (Applied Biosystems, Inc., Foster City, Calif.).

Figure 14:
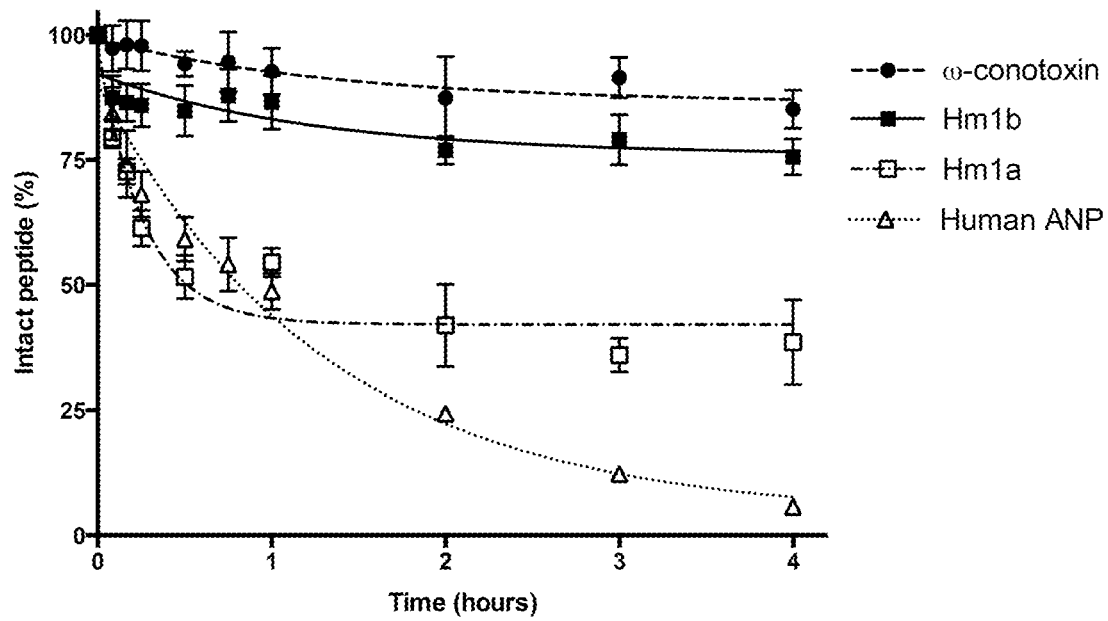
FIG. 14 Stability of Hm1a and Hm1b in cerebrospinal fluid in comparison to human atrial natriuretic peptide (ANP) and ω-conotoxin MVIA (ziconotide) over a period of 4 hours.
Figure 15:
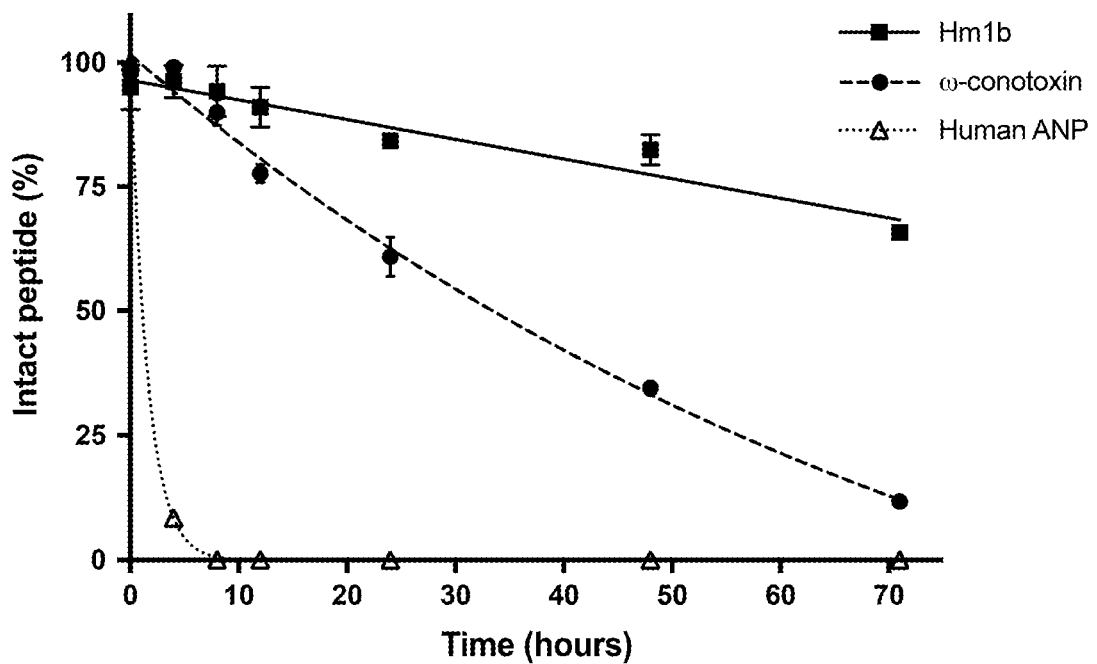
FIG. 15 Stability of Hm1b in cerebrospinal fluid in comparison to human ANP and ω-conotoxin MVIA over a period of 72 hours.

Recombinant Hm1b was significantly more stable than native Hm1a in human CSF, with approximately 80% of Hm1b remaining after four hours in comparison to approximately 45% of Hm1a (FIG. 14). Both Hm1a and Hm1b were significantly more stable than hANP, but Hm1a was less stable than ω-conotoxin MVIIA In contrast, Hm1b was significantly more stable than both hANP and ω-conotoxin MVIIA over a period of 72 hours, with approximately 65% Hm1b remaining after 72 hours in comparison to approximately 10% ω-conotoxin MVIIA and no detectable hANP (FIG. 15).

Example 10 Effect of Long-Term Hm1a Treatment on Seizure Frequency and Mortality in the Dravet Syndrome Mouse Model To determine the long-term efficacy of synthetic Hm1a (Example 1), 24 hours after ICV guide cannula surgery performed as per Example 5, a cohort of Dravet syndrome mice were administered Hm1a (0.5 μM in 0.1% bovine serum albumin in sterile saline) or vehicle (0.1% bovine serum albumin in sterile saline) continuously at a rate of 0.2 L/minute for up to five days using syringe and driver as previously described in Example 5 (n=4). Seizure frequency was measured using continuous video recordings of unrestrained animals from P18 to P23.

Figure 16:
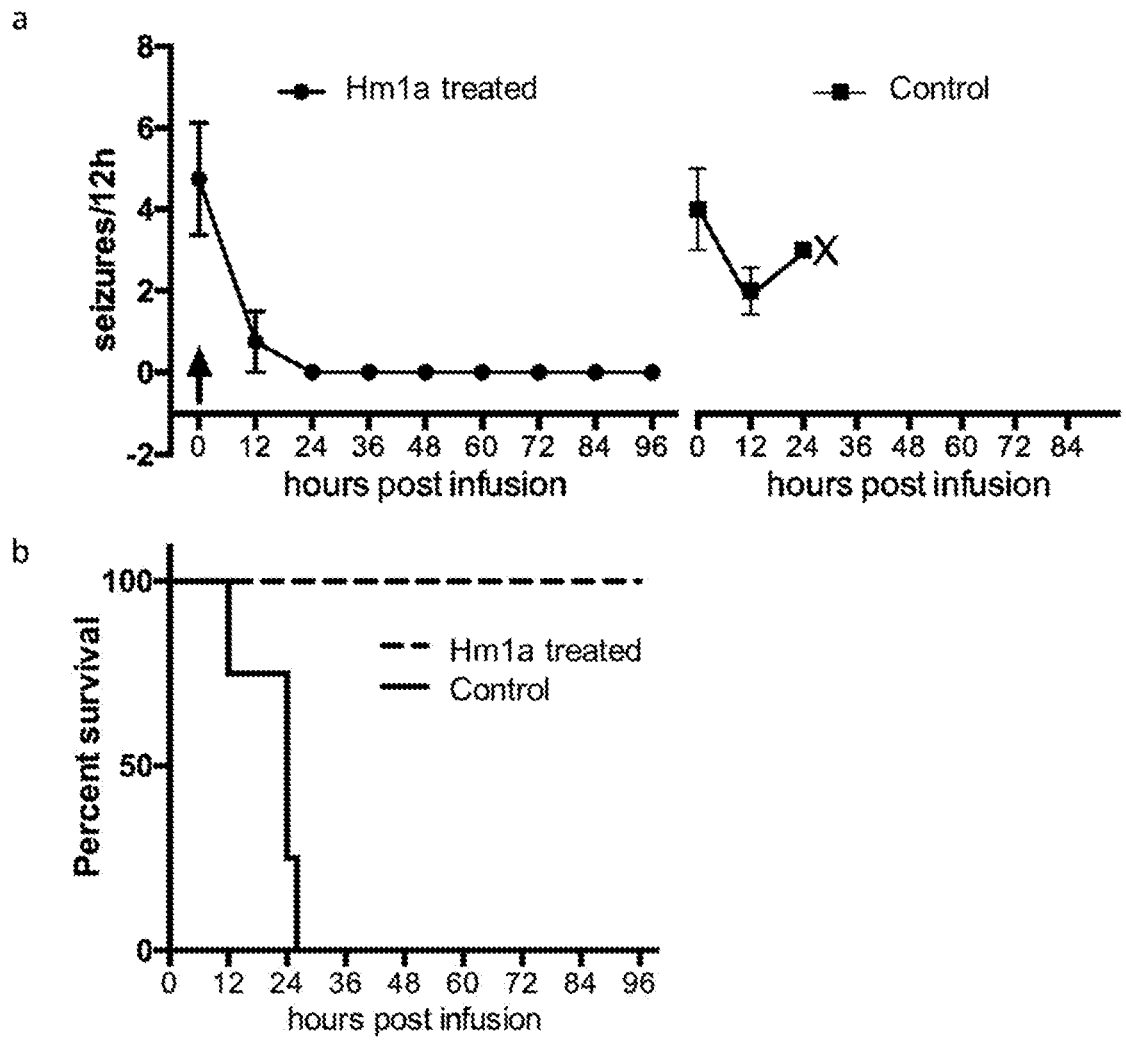
FIG. 16 Effect of long-term Hm1a treatment on seizures and post-ictal mortality in Dravet syndrome mouse model. a. Seizure count during 24 hours prior to infusion (indicated as day 0) for SCN1A knock-out Hm1a-treated mice (●) and control group (■) (n=4). Intracerebroventricular (ICV) infusion of Hm1a commenced at the time indicated by the arrow and was delivered continuously for 4 days (96 hrs). Data is presented as mean±standard error. The "X" indicates that control animals did not survive beyond the 24 h time point. b. Survival curve of Hm1a-treated mice in comparison to control SCN1A knock-out mice.

Hm1a was infused during the critical window from P19 to P23, when the highest rate of ictal events and mortality occurs in the Dravet syndrome model (Yamakawa (2011) *Epilepsia*, 52(s2): 70-71). Seizures were abolished following Hm1a administration and these animals remained seizure free for the duration of the experiment (FIG. 16a, left panel), in comparison to control animals which experienced ongoing seizures (FIG. 16a, right panel). Moreover, control animals treated with vehicle only all died within 26 hours, whereas there was no mortality in the cohort of animals treated with Hm1a (FIG. 16b).

The claims defining the invention are as follows:

1. A method of enhancing $Na_v1.1$ activity, comprising contacting a $Na_v1.1$ expressing cell with an isolated, synthetic or recombinant peptide comprising, consisting or consisting essentially of SEQ ID NO: 1:

[SEQ ID NO: 1]
$Xaa_1CRYLFGGCXaa_2Xaa_3TXaa_4DCCKHLXaa_5CRXaa_6DXaa_7Xaa_8YCZ_1$ wherein:
$Xaa_1$ is absent or is selected from acidic amino acid residues, including Asp and Glu;
$Xaa_2$ is selected from small amino acid residues, including Ser and Thr, and basic amino acid residues, including Arg, His and Lys;
$Xaa_3$ is selected from selected from small amino acid residues, including Ser and Thr;
$Xaa_4$ is selected from small amino acid residues, including Ser, Thr, Ala and Gly;
$Xaa_5$ is selected from small amino acid residues, including Ser, Thr, Ala and Gly;
$Xaa_6$ is selected from small amino acid residues, including Ser and Thr;
$Xaa_7$ is selected from aromatic amino acid residues, including Phe, Trp and Tyr, and hydrophobic amino acid residues, including Ile, Leu and Val;
$Xaa_8$ is selected from aromatic amino acid residues, including Phe, Trp and Tyr, and basic amino acid residues, including Arg, His and Lys; and
$Z_1$ is absent or is an amino acid sequence of SEQ ID NO: 2:

[SEQ ID NO: 2]
$AWDGTFXaa_9$ wherein:
$Xaa_9$ is absent or is a small amino acid residue, including Ser and Thr;
wherein the peptide is other than a peptide consisting of the amino acid sequence of SEQ ID NO: 4:

[SEQ ID NO: 4]
ECRYLFGGCSSTSDCCKHLSCRSDWKYCAWDGTFS.

2. A method of treating or preventing a condition in respect of which enhancing $Na_v1.1$ activity is associated with effective treatment, comprising administration of an isolated, synthetic or recombinant peptide comprising, consisting or consisting essentially of SEQ ID NO: 1:

[SEQ ID NO: 1]
$Xaa_1CRYLFGGCXaa_2Xaa_3TXaa_4DCCKHLXaa_5CRXaa_6DXaa_7Xaa_8YCZ_1$ wherein:
$Xaa_1$ is absent or is selected from acidic amino acid residues, including Asp and Glu;
$Xaa_2$ is selected from small amino acid residues, including Ser and Thr, and basic amino acid residues, including Arg, His and Lys;
$Xaa_3$ is selected from selected from small amino acid residues, including Ser and Thr;
$Xaa_4$ is selected from small amino acid residues, including Ser, Thr, Ala and Gly;
$Xaa_5$ is selected from small amino acid residues, including Ser, Thr, Ala and Gly;
$Xaa_6$ is selected from small amino acid residues, including Ser and Thr;
$Xaa_7$ is selected from aromatic amino acid residues, including Phe, Trp and Tyr, and hydrophobic amino acid residues, including Ile, Leu and Val;
$Xaa_8$ is selected from aromatic amino acid residues, including Phe, Trp and Tyr, and basic amino acid residues, including Arg, His and Lys; and
$Z_1$ is absent or is an amino acid sequence of SEQ ID NO: 2:

[SEQ ID NO: 2]
$AWDGTFXaa_9$ wherein:
$Xaa_9$ is absent or is a small amino acid residue, including Ser and Thr.

3. The method according to claim 2, wherein the condition is epilepsy or Alzheimer's disease.

4. The method according to claim 3, wherein the epilepsy is selected from Dravet syndrome, generalised epilepsy with febrile seizures plus, borderline severe myoclonic epilepsy of infancy and intractable childhood epilepsy with generalised tonic-clonic seizures.

5. The method according to claim 4, wherein the epilepsy is Dravet syndrome.

6. The method according to claim 2, wherein $Xaa_1$ is Glu.

7. The method according to claim 2, wherein $Xaa_2$ is Lys or Ser.

8. The method according to claim 2, wherein $Xaa_4$ is Ser or Ala.

9. The method according to claim 2, wherein $Xaa_5$ is Gly or Ser.

10. The method according to claim 2, wherein $Xaa_7$ is Leu or Trp.

11. The method according to claim 2, wherein $Xaa_8$ is Lys or Tyr.

12. The method according to claim 2, wherein $Z_1$ is the amino acid sequence of SEQ ID NO: 2.

13. The method according to claim 2, wherein $Xaa_9$ is Ser.

14. The method according to claim 2, wherein the peptide of SEQ ID NO: 1 comprises, consists or consists essentially of the amino acid sequence of SEQ ID NO: 4 or 5:

[SEQ ID NO: 4]
ECRYLFGGCSSTSDCCKHLSCRSDWKYCAWDGTFS
or

[SEQ ID NO: 5]
ECRYLFGGCKTTADCCKHLGCRTDLYYCAWDGTF.

15. The method according to claim 2, wherein the six cysteine residues in the peptide are bonded in pairs to form three disulfide bonds.

16. The method according to claim 15, wherein the disulfide bonds are formed between the side chains of Cys 2 and Cys 16, Cys 9 and Cys 21, and Cys 15 and Cys 28.

17. An isolated, synthetic or recombinant peptide comprising, consisting or consisting essentially of SEQ ID NO: 1:

[SEQ ID NO: 1]
$Xaa_1CRYLFGGCXaa_2Xaa_3TXaa_4DCCKHLXaa_5CRXaa_6DXaa_7Xaa_8YCZ_1$ wherein
$Xaa_1$ is absent or is selected from acidic amino acid residues, including Asp and Glu;
$Xaa_2$ is selected from small amino acid residues, including Ser and Thr, and basic amino acid residues, including Arg, His and Lys;
$Xaa_3$ is selected from selected from small amino acid residues, including Ser and Thr;

Xaa₄ is selected from small amino acid residues, including Ser, Thr, Ala and Gly;

Xaa₅ is selected from small amino acid residues, including Ser, Thr, Ala and Gly;

Xaa₆ is selected from small amino acid residues, including Ser and Thr;

Xaa₇ is selected from aromatic amino acid residues, including Phe, Trp and Tyr, and hydrophobic amino acid residues, including Ile, Leu and Val;

Xaa₈ is selected from aromatic amino acid residues, including Phe, Trp and Tyr, and basic amino acid residues, including Arg, His and Lys;

Z₁ is absent or is an amino acid sequence of SEQ ID NO: 2:

```
                              [SEQ ID NO: 2]
AWDGTFXaa₉
``` wherein:

Xaa₉ is absent or is a small amino acid residue, including Ser and Thr; and wherein the peptide is other than a peptide consisting of the amino acid sequence of SEQ ID NO: 4, SEQ ID NO: 5 and SEQ ID NO: 10:

```
                              [SEQ ID NO: 4]
ECRYLFGGCSSTSDCCKHLSCRSDWKYCAWDGTFS

[SEQ ID NO: 5]
ECRYLFGGCKTTADCCKHLGCRTDLYYCAWDGTF

[SEQ ID NO: 10]
ECRYLFGGCKTTADCCKHLGCRTDLYYCAWDGTF-NH₂.
```

18. The peptide according to claim 17, wherein Xaa₁ is Glu.

19. The peptide according to claim 17, wherein Xaa₂ is Lys or Ser.

20. The peptide according to claim 17, wherein Xaa₄ is Ser or Ala.

21. The peptide according to claim 17, wherein Xaa₅ is Gly or Ser.

22. The peptide according to claim 17, wherein Xaa₇ is Leu or Trp.

23. The peptide according to claim 17, wherein Xaa₈ is Lys or Tyr.

24. The peptide according to claim 17, wherein $Z_a$ is the amino acid sequence of SEQ ID NO: 2.

25. The peptide according to claim 17, wherein Xaa₉ is absent.

26. The peptide according to claim 17, wherein the peptide comprises, consists or consists essentially of the amino acid sequence of SEQ ID NO: 8:

```
                              [SEQ ID NO: 8]
SECRYLFGGCKTTADCCKHLGCRTDLYYCAWDGTF.
```

27. The peptide according to claim 17, wherein the six cysteine residues are bonded in pairs to form three disulfide bonds.

28. The peptide according to claim 27, wherein the disulfide bonds are formed between the side chains of Cys 2 and Cys 16, Cys 9 and Cys 21, and Cys 15 and Cys 28.

29. A composition comprising a peptide according to claim 17 and a pharmaceutically acceptable carrier or diluent.

* * * * *

SEQUENCE LISTING

<160> NUMBER OF SEQ ID NOS: 12

<210> SEQ ID NO 1
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent or is selected from acidic amino
      acid residues, including Asp and Glu
<220> FEATURE:
<221> NAME/KEY: MISC_FEATURE
<222> LOCATION: (10)..(10)
<223> OTHER INFORMATION: Xaa is selected from small amino acid residues,
      including Ser and Thr, and basic amino acid residues, including
      Arg, His and Lys
<220> FEATURE:
<221> NAME/KEY: MISC_FEATURE
<222> LOCATION: (11)..(11)
<223> OTHER INFORMATION: Xaa is selected from small amino acid residues,
      including Ser and Thr
<220> FEATURE:
<221> NAME/KEY: MISC_FEATURE
<222> LOCATION: (13)..(13)
<223> OTHER INFORMATION: Xaa is selected from small amino acid residues,
      including Ser, Thr, Ala and Gly
<220> FEATURE:
<221> NAME/KEY: MISC_FEATURE
<222> LOCATION: (20)..(20)
<223> OTHER INFORMATION: Xaa is selected from small amino acid residues,
      including Ser, Thr, Ala and Gly
<220> FEATURE:
<221> NAME/KEY: MISC_FEATURE
<222> LOCATION: (23)..(23)
<223> OTHER INFORMATION: Xaa is selected from small amino acid residues,
      including Ser and Thr
<220> FEATURE:
<221> NAME/KEY: MISC_FEATURE
<222> LOCATION: (25)..(25)
<223> OTHER INFORMATION: Xaa is selected from aromatic amino acid
      residues, including Phe, Trp and Tyr, and hydrophobic amino acid
      residues, including Ile, Leu and Val
<220> FEATURE:
<221> NAME/KEY: MISC_FEATURE
<222> LOCATION: (26)..(26)
<223> OTHER INFORMATION: Xaa is selected from aromatic amino acid
      residues, including Phe, Trp and Tyr, and basic amino acid
      residues, including Arg, His and Lys
<220> FEATURE:
<221> NAME/KEY: MISC_FEATURE
<222> LOCATION: (29)..(29)
<223> OTHER INFORMATION: Xaa is absent or is an amino acid sequence of
      SEQ ID NO: 2

<400> SEQUENCE: 1

Xaa Cys Arg Tyr Leu Phe Gly Gly Cys Xaa Xaa Thr Xaa Asp Cys Cys
1               5                   10                  15

Lys His Leu Xaa Cys Arg Xaa Asp Xaa Xaa Tyr Cys Xaa
            20                  25

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa is absent or is a small amino acid residue,
      including Ser and Thr

```
<400> SEQUENCE: 2

Ala Trp Asp Gly Thr Phe Xaa
1               5

<210> SEQ ID NO 3
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa is selected from small amino acid residues,
      including Ser and Thr, and basic amino acid residues, including
      Arg, His and Lys
<220> FEATURE:
<221> NAME/KEY: MISC_FEATURE
<222> LOCATION: (11)..(11)
<223> OTHER INFORMATION: Xaa is selected from small amino acid residues,
      including Ser and Thr
<220> FEATURE:
<221> NAME/KEY: MISC_FEATURE
<222> LOCATION: (13)..(13)
<223> OTHER INFORMATION: Xaa is selected from small amino acid residues,
      including Ser, Thr, Ala and Gly
<220> FEATURE:
<221> NAME/KEY: MISC_FEATURE
<222> LOCATION: (20)..(20)
<223> OTHER INFORMATION: Xaa is selected from small amino acid residues,
      including Ser, Thr, Ala and Gly
<220> FEATURE:
<221> NAME/KEY: MISC_FEATURE
<222> LOCATION: (23)..(23)
<223> OTHER INFORMATION: Xaa is selected from small amino acid residues,
      including Ser and Thr
<220> FEATURE:
<221> NAME/KEY: MISC_FEATURE
<222> LOCATION: (25)..(25)
<223> OTHER INFORMATION: Xaa is selected from aromatic amino acid
      residues, including Phe, Trp and Tyr, and hydrophobic amino acid
      residues, including Ile, Leu and Val
<220> FEATURE:
<221> NAME/KEY: MISC_FEATURE
<222> LOCATION: (26)..(26)
<223> OTHER INFORMATION: Xaa is selected from aromatic amino acid
      residues, including Phe, Trp and Tyr, and basic amino acid
      residues, including Arg, His and Lys
<220> FEATURE:
<221> NAME/KEY: MISC_FEATURE
<222> LOCATION: (35)..(35)
<223> OTHER INFORMATION: Xaa is absent or is a small amino acid residue,
      including Ser and Thr

<400> SEQUENCE: 3

Glu Cys Arg Tyr Leu Phe Gly Gly Cys Xaa Xaa Thr Xaa Asp Cys Cys
1               5                   10                  15

Lys His Leu Xaa Cys Arg Xaa Asp Xaa Xaa Tyr Cys Ala Trp Asp Gly
            20                  25                  30

Thr Phe Xaa
        35

<210> SEQ ID NO 4
<211> LENGTH: 35
<212> TYPE: PRT
<213> ORGANISM: Heteroscodra maculata

<400> SEQUENCE: 4

Glu Cys Arg Tyr Leu Phe Gly Gly Cys Ser Ser Thr Ser Asp Cys Cys
1               5                   10                  15

Lys His Leu Ser Cys Arg Ser Asp Trp Lys Tyr Cys Ala Trp Asp Gly
```

Thr Phe Ser
        35

<210> SEQ ID NO 5
<211> LENGTH: 34
<212> TYPE: PRT
<213> ORGANISM: Heteroscodra maculata

<400> SEQUENCE: 5

Glu Cys Arg Tyr Leu Phe Gly Gly Cys Lys Thr Thr Ala Asp Cys Cys
1               5                   10                  15

Lys His Leu Gly Cys Arg Thr Asp Leu Tyr Tyr Cys Ala Trp Asp Gly
            20                  25                  30

Thr Phe

<210> SEQ ID NO 6
<211> LENGTH: 34
<212> TYPE: PRT
<213> ORGANISM: Artificial Sequence
<220> FEATURE:
<223> OTHER INFORMATION: Synthetic

<400> SEQUENCE: 6

Glu Cys Arg Tyr Leu Phe Gly Gly Cys Ser Thr Thr Ala Asp Cys Cys
1               5                   10                  15

Lys His Leu Gly Cys Arg Thr Asp Leu Tyr Tyr Cys Ala Trp Asp Gly
            20                  25                  30

Thr Phe

<210> SEQ ID NO 7
<211> LENGTH: 36
<212> TYPE: PRT
<213> ORGANISM: Artificial Sequence
<220> FEATURE:
<223> OTHER INFORMATION: Synthetic

<400> SEQUENCE: 7

Ser Glu Cys Arg Tyr Leu Phe Gly Gly Cys Ser Ser Thr Ser Asp Cys
1               5                   10                  15

Cys Lys His Leu Ser Cys Arg Ser Asp Trp Lys Tyr Cys Ala Trp Asp
            20                  25                  30

Gly Thr Phe Ser
        35

<210> SEQ ID NO 8
<211> LENGTH: 35
<212> TYPE: PRT
<213> ORGANISM: Artificial Sequence
<220> FEATURE:
<223> OTHER INFORMATION: Synthetic

<400> SEQUENCE: 8

Ser Glu Cys Arg Tyr Leu Phe Gly Gly Cys Lys Thr Thr Ala Asp Cys
1               5                   10                  15

Cys Lys His Leu Gly Cys Arg Thr Asp Leu Tyr Tyr Cys Ala Trp Asp
            20                  25                  30

Gly Thr Phe
        35

<210> SEQ ID NO 9

```
<211> LENGTH: 35
<212> TYPE: PRT
<213> ORGANISM: Artificial Sequence
<220> FEATURE:
<223> OTHER INFORMATION: Synthetic

<400> SEQUENCE: 9

Ser Glu Cys Arg Tyr Leu Phe Gly Gly Cys Ser Thr Thr Ala Asp Cys
1               5                   10                  15

Cys Lys His Leu Gly Cys Arg Thr Asp Leu Tyr Tyr Cys Ala Trp Asp
            20                  25                  30

Gly Thr Phe
        35

<210> SEQ ID NO 10
<211> LENGTH: 34
<212> TYPE: PRT
<213> ORGANISM: Heteroscodra maculata
<220> FEATURE:
<221> NAME/KEY: MOD_RES
<222> LOCATION: (34)..(34)
<223> OTHER INFORMATION: AMIDATION

<400> SEQUENCE: 10

Glu Cys Arg Tyr Leu Phe Gly Gly Cys Lys Thr Thr Ala Asp Cys Cys
1               5                   10                  15

Lys His Leu Gly Cys Arg Thr Asp Leu Tyr Tyr Cys Ala Trp Asp Gly
            20                  25                  30

Thr Phe

<210> SEQ ID NO 11
<211> LENGTH: 34
<212> TYPE: PRT
<213> ORGANISM: Artificial Sequence
<220> FEATURE:
<223> OTHER INFORMATION: Partial sequence of Hm1a from Edman sequencing

<400> SEQUENCE: 11

Glu Cys Arg Tyr Leu Phe Gly Gly Cys Ser Ser Thr Ser Asp Cys Cys
1               5                   10                  15

Lys His Leu Ser Cys Arg Ser Asp Trp Lys Tyr Cys Ala Trp Asp Gly
            20                  25                  30

Thr Phe

<210> SEQ ID NO 12
<211> LENGTH: 33
<212> TYPE: PRT
<213> ORGANISM: Artificial Sequence
<220> FEATURE:
<223> OTHER INFORMATION: Partial sequence of Hm1b from Edman sequencing

<400> SEQUENCE: 12

Glu Cys Arg Tyr Leu Phe Gly Gly Cys Lys Thr Thr Ala Asp Cys Cys
1               5                   10                  15

Lys His Leu Gly Cys Arg Thr Asp Leu Tyr Tyr Cys Ala Trp Asp Gly
            20                  25                  30

Thr
```